United States Patent
Chapdelaine et al.

(10) Patent No.: US 7,189,714 B2
(45) Date of Patent: Mar. 13, 2007

(54) N-TYPE CALCIUM CHANNEL ANTAGONISTS FOR THE TREATMENT OF PAIN

(75) Inventors: Marc Chapdelaine, Wilmington, DE (US); Lucius Kemp, Philadelphia, PA (US); John McCauley, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 382 days.

(21) Appl. No.: 10/415,853

(22) PCT Filed: Oct. 31, 2001

(86) PCT No.: PCT/SE01/02389

§ 371 (c)(1),
(2), (4) Date: Nov. 3, 2003

(87) PCT Pub. No.: WO02/36567

PCT Pub. Date: May 10, 2002

(65) Prior Publication Data

US 2004/0077644 A1     Apr. 22, 2004

(30) Foreign Application Priority Data

Nov. 6, 2000  (SE)  .................................... 0004054

(51) Int. Cl.
A61K 31/5377 (2006.01)
A61K 31/506 (2006.01)
A61K 31/472 (2006.01)
A61K 31/4725 (2006.01)
C07D 265/30 (2006.01)
C07D 239/04 (2006.01)

(52) U.S. Cl. ................ 514/233.5; 514/235.8; 514/236.8; 514/256; 514/313; 544/128; 544/149; 544/152; 544/333; 546/159

(58) Field of Classification Search ............... 514/311, 514/233.5, 235.8, 236.8, 256, 313; 544/63, 544/224, 128, 149, 152, 333; 546/152, 159
See application file for complete search history.

(56) References Cited

U.S. PATENT DOCUMENTS 2,568,778 A * 9/1951 Surrey et al. ............... 546/175

FOREIGN PATENT DOCUMENTS

EP  1072263 A1  1/2001
GB   794043 A   4/1958

OTHER PUBLICATIONS

Moyer et al., The synthesis and identification of 4,6-diaminoquinoline derivatives as potent immunostimulants. Bioorganic & Medicinal Chemistry Letters, vol. 2 (No. 12), pp. 1589-1594, (Apr. 8, 1992).*

Mikel P. Moyer et al., "The synthesis and identification of 4,6-diaminoquinoline derivatives as potent immunostimulants," Bioorganic & Medicinal Chemistry Letters, vol. 2 (No. 12), p. 1589-1594, (Apr. 8, 1992.).

L. V. Gyul'Budagyan et al., "Derivatives of 2-(p-methoxyphenyl)-6-aminoquinoline," Chemical Abstracts, vol. 66 (No. 13), p. 5224, (Mar. 27, 1967).

* cited by examiner

Primary Examiner—Kamal A. Saeed
Assistant Examiner—Michael P. Barker
(74) Attorney, Agent, or Firm—Kenneth F. Mitchell; Cozen O'Connor, P.C.

(57) ABSTRACT

Compounds useful for the treatment of pain in accord with the following structural diagram,

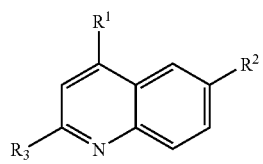

wherein $R^1$, $R^2$ and $R^3$ are any of a number of groups as defined in the specification and pharmaceutical compositions and methods of treatment utilising such compounds.

14 Claims, No Drawings

N-TYPE CALCIUM CHANNEL ANTAGONISTS FOR THE TREATMENT OF PAIN

CROSS-REFERENCE TO RELATED APPLICATIONS

This application is the U.S. National Stage filing of International Application Serial No. PCT/SE01/02389 filed Oct. 31, 2001, which claims priority to SE 0004054-3 filed Nov. 6, 2000, each of which is incorporated herein by reference in its entirety.

FIELD OF THE INVENTION

This invention relates to compounds and methods for the treatment or prevention of pain or nociception.

RELATED ART

Pain causes a great deal of suffering and is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult. Where pain is "caused" by the stimulation of nociceptive receptors and transmitted over intact neural pathways, this is termed nociceptive pain. Pain may also be caused by damage to neural structures, and pain is often is manifested as neural supersensitivity; this type of pain is referred to as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anaesthetics which obtund pain by producing a hiatus in consciousness, or local anaesthetics which block transmission in peripheral nerve fibres thereby preventing pain.

Tachykinin antagonists have been reported to induce antinociception in animals, which is believed to be analogous to analgesia in man (for review see Maggi et al, J. Auton. Pharmacol. (1993) 13, 23–93). In particular, non-peptide NK-1 receptor antagonists have been shown to produce such analgesia, thus, for example, in classical tests of chemo-nociception (phenylbenzoquinone-induced writhing and formalin test) the NK-1 receptor antagonist RP 67,580 produced analgesia with potency comparable to that of morphine (Garret et al, Proc. Natl. Acad. Sci. USA (1993) 88, 10208–10212).

Opioid analgesics are a well-established class of analgesic agents. These compounds are generally accepted to include, in a generic sense, all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonise the analgesic effects of morphine, when given alone it can be a potent analgesic in its own right. Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds.

Anti-inflammatory compounds directed at blocking or reducing synovial inflammation, and thereby improving function, and analgesics directed to reducing pain, are presently the primary method of treating the rheumatoid diseases and arthritis. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to J. Hosp. Pharm., 36:622 (May 1979).

Calcium channels are membrane-spanning, multi-subunit proteins that allow controlled entry of $Ca^{++}$ ions into cells from the extracellular fluid. Such channels are found throughout the animal kingdom, and have been identified in bacterial, fungal and plant cells. Commonly, calcium channels are voltage dependent. In such channels, the "opening" allows an initial influx of $Ca^{++}$ ions into the cells which lowers the potential difference between the inside of the cell bearing the channel and the extracellular medium bathing the cell. The rate of influx of $Ca^{++}$ ions into the cell depends on this potential difference. All "excitable" cells in animals, such as neurons of the central nervous system ("CNS"), peripheral nerve cells, and muscle cells, including those of skeletal muscles, cardiac muscles, and venous and arterial smooth muscles, have voltage-dependent calcium channels. Calcium channels are physiologically important because the channels have a central role in regulating intracellular $Ca^{++}$ ions levels. These levels are important for cell viability and function. Thus, intracellular $Ca^{++}$ ion concentrations are implicated in a number of vital processes in animals, such as neurotransmitter release, muscle contraction, pacemaker activity, and secretion of hormones.

It is believed that calcium channels are relevant in certain disease states. A number of compounds useful in treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{++}$ ions into the cells in response to depolarization of the cell membrane. An understanding of the pharmacology of compounds that interact with calcium channels in other organ systems, such as the central nervous system, and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

Multiple types of calcium channels have been detected based on electrophysiological and pharmacological studies of various mammalian cells from various tissues (e.g., skeletal muscle, cardiac muscle, lung, smooth muscle and brain) Bean, B. P., Annu Rev. Physiol. 51:367–384 (1989) and Hess, P., Annu. Rev. Neurosci. 56:337 (1990). These different types of calcium channels have been broadly categorized into four classes, L-, T-, N-, and P-type, distinguished by current kinetics, holding potential sensitivity and, sensitivity to calcium channel agonists and antagonists. Four subtypes of neuronal voltage-dependent calcium channels have been proposed Swandulla, D. et al., Trends Neurosci 14:46 (1991). The L-, N- and P-type channels have each been implicated in nociception, but only the N-type channel has been consistently implicated in acute, persistent and neuropathic pain. A synthetic version of ω-conotoxin MVIIA, a 25-amino acid peptide derived from the venom of the piscivorous marine snail, *Conus magus* has been used intrathecally in humans and has ~85% success rate for the treatment of pain with a greater potency than morphine.

While known drug therapies have utility, there are drawbacks to their use. For instance, it may take up to six months of consistent use of some medications in order for the product to have effect in relieving the patient's pain. Consequently, a particular subject may be receiving treatment and continuing to suffer for up to six months before the physician can assess whether the treatment is effective. Many existing drugs also have substantial adverse side effects in certain patients, and subjects must therefore be carefully monitored. Additionally, most existing drugs bring only temporary relief to sufferers and must be taken consistently on a daily or weekly basis for continued relief. Finally, with disease progression, the amount of medication needed to alleviate the pain may increase thus increasing the potential for side effects. Thus, there is still a need for an effective and safe treatment to alleviate pain.

SUMMARY OF THE INVENTION

In one aspect the present invention provides compounds having selective action at N-type calcium channels that are useful for the treatment of pain.

Compounds of the present invention that show selective action at N-type calcium channels are compounds in accord with structural diagram I,

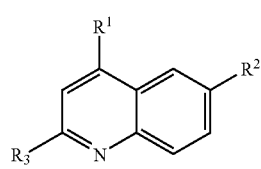

I wherein, $R^1$ is selected from $E^1$ and $E^2$ wherein:

$E^1$ is $N(R^4)_2$ where $R^4$ at each occurrence is selected from hydrogen, benzyl, $C_{1-6}$alkyl, $C_{3-7}$cycloalkyl, methoxy$C_{1-4}$alkyl, and $E^2$ is an N-linked heterocyclyl selected from piperidinyl, morpholinyl and pyrrolidinyl;

$R^2$ is selected from $E^3$ and $E^4$, wherein:

$E^3$ is $N(R^5)_2$ where $R^5$ at each occurrence is independently selected from hydrogen, $C_{1-6}$alkyl, phenyl$C_{1-6}$alkyl, $C_{1-6}$alkenyl, $C_{3-7}$cycloalkyl, 1-methyl-$C_{3-7}$cycloalkyl, $C_{1-6}$alkylcarbonyl, $C_{1-6}$alkoxycarbonyl, tetrahydrofurfuryl, adamantyl, pyridyl, benzthiazolyl, pyrazolyl, 1,3-isoindoledion-5-yl, phenyl substituted pyrazolyl, pyrimidinyl and phenyl mono- or di-substituted with a moiety independently selected at each occurrence from $C_{1-6}$alkoxy, $C_{1-6}$alkyl, perhalo$C_{1-6}$alkyl, halogen and morpholinyl, and $E^4$ is selected from nitro, or an N-linked heterocyclyl selected from piperidinyl, morpholinyl and pyrrolidinyl, and $R^3$ is selected from $C_{1-6}$alkyl, phenoxy$C_{1-3}$alkyl or phenyl substituted with $E^5$, where $E^5$ is selected from hydrogen, halogen, $C_{1-6}$alkoxy, $C_{3-7}$cycloalkyl, morpholinyl, $C_{1-4}$perfluoroalkyl, NH$C_{1-3}$alkyl and N($C_{1-3}$alkyl)$_2$.

Certain embodiments of the invention are compounds in accord with structural diagram I wherein $R^1$ and $R^3$ are as heretofore defined and $R^2$ is NHR$^5$, where $R^5$ is selected from benz[d]thiazol-2-yl, 1,5-dimethyl-2-phenyl-1,2-dihydropyrazol-3-on-4-yl, 2-phenyl-2,5-dihydro-1H-pyrazol-3-yl, pyrimidin-4-yl, tetrahydrofuran-2-ylmethyl, 2-phenylpropyl and 1-phenylethyl.

Other embodiments of the invention are compounds in accord with structural diagrams II, III, or IV,

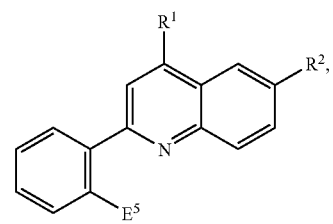

II

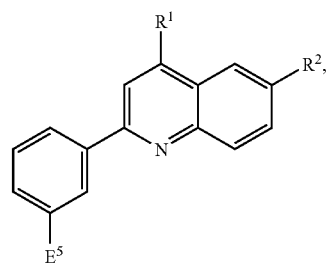

III

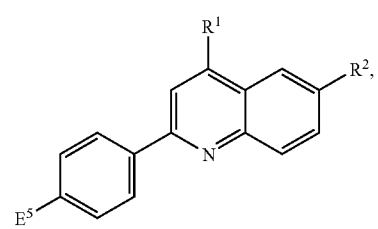

IV wherein $R^1$, $R^2$ and $E^5$ are as heretofore defined.

Yet other compounds of the invention are compounds in accord with structural diagram III where $E^5$ is halogen and $R^1$ and $R^2$ are as heretofore defined.

Still other compounds of the invention are compounds in accord with structural diagram III where $E^5$ is fluoro and $R^1$ and $R^2$ are as heretofore defined.

Particular compounds of the invention are compounds in accord with structural diagram III where $R^1$ is $NHCH_3$ or $N(CH_3)_2$, $R^2$ is NHcyclopropyl or $NHCH_3$ and $E^5$ is fluoro.

Most particular compounds of the invention are those exemplified herein.

In another aspect, the invention comprises a method for using compounds according to structural diagram I for the treatment of pain, said method comprising administering a pain-ameliorating effective amount of any such compound.

One embodiment of the method of the invention comprises administering a pain-ameliorating effective amount of a compound in accordance with structural diagram I to a subject in need of treatment for acute, persistent or neuropathic pain.

In a further aspect, the invention comprises methods for making compounds in accord with structural diagram I.

In yet another aspect, the invention comprises pharmaceutical compositions comprising compounds in accord with structural diagram I together with excipients, diluents or stabilisers, as further disclosed herein, useful for the treatment of acute, persistent and neuropathic pain.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid.

Where compounds of the present invention possess a chiral center it is to be understood that the invention encompasses all optical isomers and diastereoisomers of such compounds.

Where compounds of the present invention can tautomerize it is to be understood that the invention encompasses all tautomeric forms of such compounds.

Where compounds of the present invention can exist in unsolvated as well as solvated forms such as, for example, hydrated forms, it is to be understood that the invention encompasses all such solvated and unsolvated forms.

Another aspect of the invention provides processes for making compounds of the invention, as follows:

a) Preparing novel 3-substituted-3-oxo-propionic acid ethyl esters (β-keto esters) according to structural diagram V, as follows:

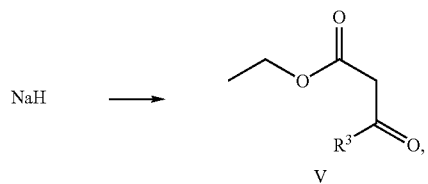

wherein $R^3$ is as heretofore defined;

b) converting said β-keto esters of structural diagram V to enamines according to structural diagram VI, as follows

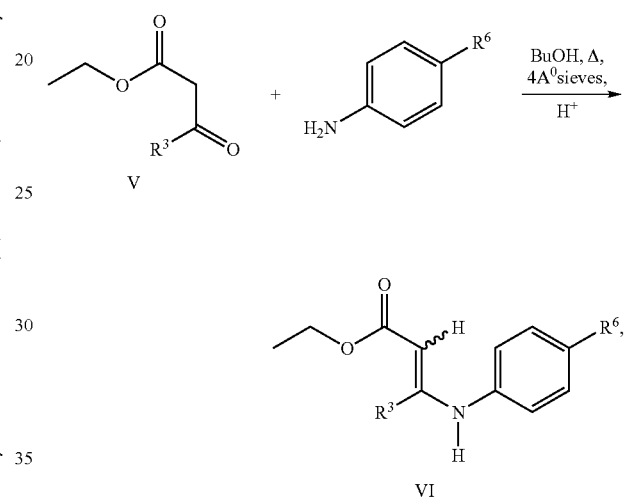

wherein $R^6$ is a group selected from $-NH-CO-CH_3$, $NO_2$ and Br;

c) cyclizing said enamines of structural diagram VI to form compounds according to structural diagram VII, as follows

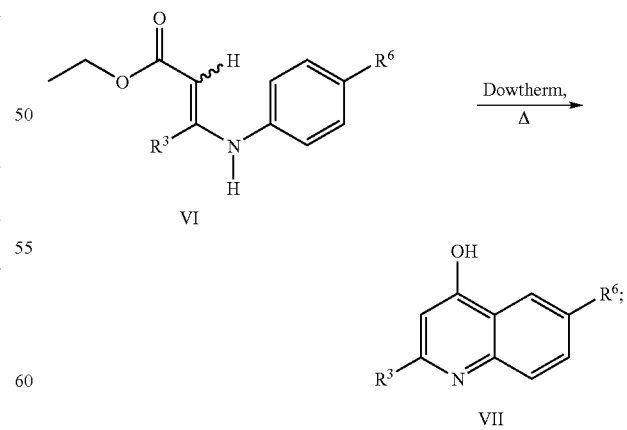

d) when $R^6$ is $-NH-CO-CH_3$, converting a compound of structural diagram VII to a compound according to structural diagram I by the process of the following scheme:

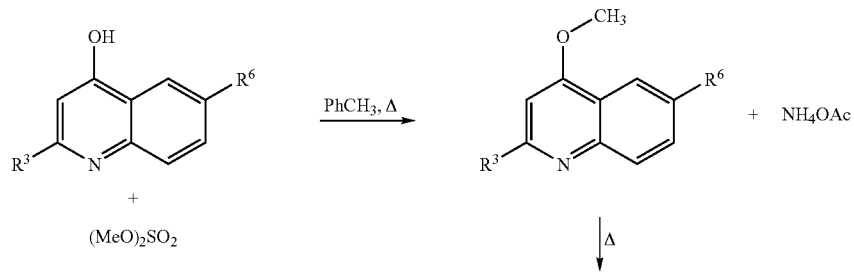
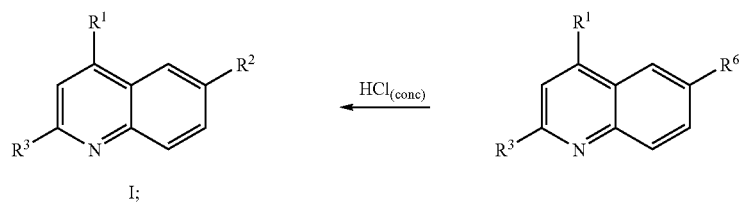
or,
when R⁶ is —NO₂, converting a compound of structural diagram VII to a compound according to structural diagram I wherein R¹ and R² are both NH₂, by the process of the following scheme:
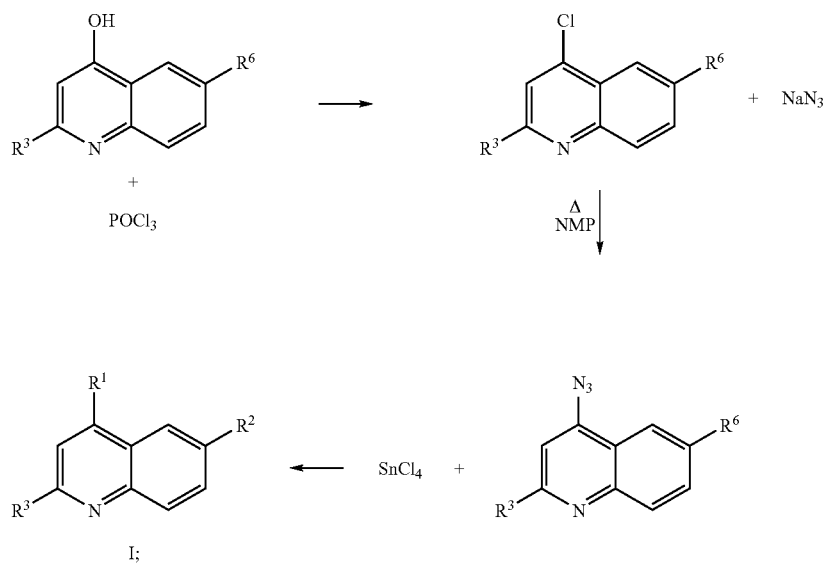

or, when $R^6$ is —Br, converting a compound of structural diagram VII to a compound according to structural diagram I wherein $R^2$ is $E^3$, by the process of the following scheme:

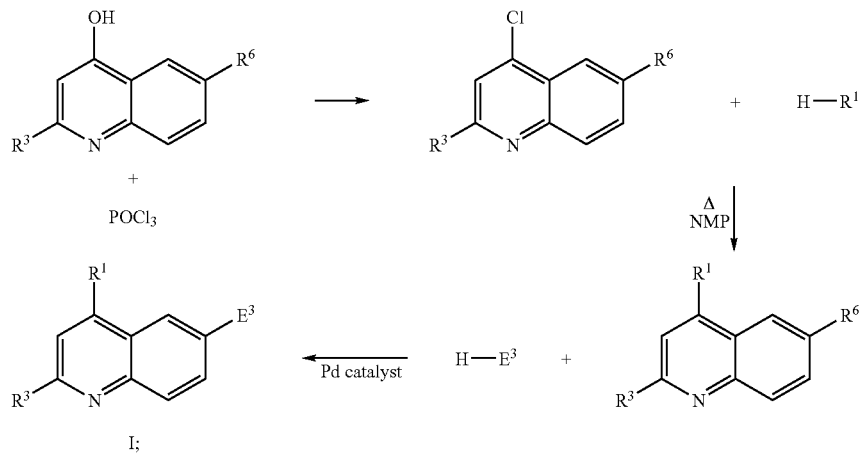

I;

wherein, if necessary, in steps a), b), c) and d) any functional group is protected with a protecting group, and thereafter, e) removing any said protecting group;

f) converting one compound according to structural diagram I to another compound according to structural diagram I by procedures described in Methods A through L herein, and g) purifying said compound of structural diagram I to the extent necessary and, if necessary, forming a pharmaceutically-acceptable salt.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition. Accordingly, a further aspect of the invention provides a pharmaceutical composition which contains a compound of the structural diagram I as defined herein or a pharmaceutically-acceptable salt thereof, in association with a pharmaceutically-acceptable additive such as an excipient or carrier.

Suitable pharmaceutical compositions that contain a compound of the invention may be administered in conventional ways, for example by oral, topical, parenteral, buccal, nasal, vaginal or rectal administration, or by inhalation. For these purposes a compound of the invention may be formulated by means known in the art in the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention, a pharmaceutical composition of this invention may also contain one or more other pharmacologically-active agents. Alternatively, a pharmaceutical composition comprising a compound of this invention may be co-administered simultaneously or sequentially with one or more other compatible pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A yet further embodiment of the invention provide the use of a compound of the structural diagram I, or a pharmaceutically-acceptable salt thereof, in the manufacture of a medicament useful for binding to N-type calcium channels in a warm-blooded animal such as a human being.

Still another embodiment of the invention provides a method of binding a compound of the invention to N-type calcium channels of a warm-blooded animal, such as a human being, in need of treatment for pain, which method comprises administering to said animal an effective amount of a compound of structural diagram I or a pharmaceutically-acceptable salt thereof.

A further aspect of the present invention provides a pharmaceutical composition which includes a compound of the present invention as defined herein or a pharmaceutically-acceptable salt thereof, in association with a pharmaceutically-acceptable additive such as an excipient or a carrier.

A still further aspect of the present invention is a method of treatment of the human or animal body that includes the administration of a compound of the present invention or a pharmaceutically-acceptable salt thereof.

Definitions:

When used herein "halo" or "halogen" means fluoro, chloro, bromo or iodo;

when substituents herein are stated to be "selected from" or "independently selected from" a group of moieties, it is to be understood that included compounds are those where all substituents are the same and compounds where each substituent is different;

when used herein the term "alkyl," as in for example $C_{1-6}$alkyl, unless otherwise defined, includes both straight and branched chain alkyl groups. References to individual alkyl groups such as "propyl" mean the normal, straight chain form, that is, n-propyl;

when used herein, a term such as "$C_{1-6}$alkyl" means alkyl groups having 1, 2, 3, 4, 5 or 6 carbon atoms and collective groups such as $C_{1-4}$alkyl and includes straight and branched moieties such as methyl, ethyl, iso-propyl and t-butyl, similarly, a term such as "$C_{1-3}$alkoxy" includes particular moieties such as methoxy, ethoxy and propoxy, and terms used herein that are not otherwise defined are intended to have their conventionally-understood meaning.

The Methods and Examples which follow are intended to illustrate but not limit the invention. In the Methods and Examples, unless otherwise stated:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385);

yields are given for illustrative purposes only and are not necessarily the maximum attainable;

the structure of compounds of the invention were generally confirmed by conventional NMR and mass spectral techniques, peak multiplicities are shown thus: s, singlet; bs, broad singlet; d, doublet; AB or dd, doublet of doublets; t, triplet; dt, double of triplets; m, multiplet; bm, broad multiplet; FAB m/s data were obtained using a Platform spectrometer (supplied by Micromass) run in electrospray and, where appropriate, either positive ion data or negative ion data were collected, herein $(M+H)^+$ is provided;

purity of intermediates were was in general assessed by m/s or NMR analysis; and where used the following abbreviations have meanings as follows:

| | |
|---|---|
| DCM | is dichloromethane, |
| DMF | is N,N-dimethylformamide, |
| DMSO | is dimethylsulfoxide, |
| CDCl$_3$ | is deuterated chloroform, |
| FAB | is fast atom bombardment, |
| m/s | is mass spectroscopy or mass spectral, |
| NMR | is Nuclear Magnetic Resonance, |
| NMP | is N-methylpyrrolidinone, and |
| THF | is tetrahydrofuran. |

Biological Methods:

I. N-channel FLIPR (Fluorescent Laser Imaging Plate Reader) Assay.

The methods described herein provide a reliable FLIPR-based readout of the efficacy and potency with which test compounds inhibit calcium flux through the N-type calcium channel expressed in its native form in a human-derived neuroblastoma cell line differentiated chemically to a neuronal phenotype. The degree to which a compound at a particular concentration inhibited the N-channel calcium flux was determined by comparing the amplitude of peak calcium increase in the presence of the compound to a control 80 mM $K^+$ stimulus in wells without compound. Results obtained for this FLIPR assay were validated in two ways:

a) the N-channel specific peptide toxin, conotoxin MVIIA, showed an $IC_{50}$=3 nM (determined from fit to five-point concentration response analysis), compatible with the known literature value; and b) $IC_{50}$ values were determined for a set of 18 small molecules from chemistry lead series ($pIC_{50}$ range: 4.67–7.02).

Potency of these same test compounds as inhibitors of the N-type calcium current was also determined by direct electrophysiological measurement either in neuronally differentiated IMR-32 cells, or in freshly-isolated rat superior cervical ganglion neurons. $pIC_{50}$'s yielded by the two methodologies for the compound set were closely comparable (r=0.91; p<0.001).

A. Cell Culture.

An immortalized cell line, IMR32, derived from human neuroblastoma cells obtained from the ATCC (product #CCL-127) was used for all experiments. Cells were grown in T75 flasks containing Eagle's minimum essential medium (MEM) w/Earle's salts and nonessential amino acids without glutamine (Cat.#SLM-034-B, Specialty Media, Philipsburg, N.J.), 10% FBS and 1% glutamine. Cells were grown to ~70–80% confluency (by visual microscopic estimation) before sub-culturing. To maintain a stock culture, cultures were split at a ratio of 1:3–1:4 by creating a cell suspension by trituration, and pipetting a volume of the cell suspension sufficient to yield this final ratio into new flasks containing ~20 mL of fresh media. Sub-culturing was generally performed two times per week. For preparation of 96 well plates (black-walled; Cat # 3603, Costar Co., Cambridge, Mass.), a T75 flask containing cells of desired confluency was brought up to 120 mL volume with media. Cells were then freed by trituration, and the cell suspension was plated into 12–96 well plates to yield final well volume of 100 µL.

B. Cell Differentiation to Neuronal Phenotype.

Cells were induced to differentiate in a differentiation medium consisting of: MEM, 10% FBS, 1% glutamine, 1 µM 2-butyl-cAMP (49.1 mg/100 mL media (Cat. # D-0627, Sigma Corp., St Louis, Mo.), and 2.5 mM bromo-deoxyuridine (stock: 30.7 mg/10 mL media, 25 mL of above stock/100 mL media; Sigma Cat .# B-9285). To induce differentiation, the cells were treated with differentiation media (by complete medium change) 2 days after an initial plating in 96 well plates. Confluency at this time was ~40%. A complete medium change with freshly prepared differentiating medium was subsequently performed every 2–3 days. Cells were exposed to these differentiation conditions for 6 to 11 days before being used in FLIPR experiments.

C. Standard Experimental Solutions.

Solutions of the following composition (in mM) were used in experiments (Buffers without probenicid purchased from Specialty Media (Buffers A and B: Cat. # BSS053A; Buffers C & D: Cat. # BSS056A).

Buffer A (first wash buffer): Krebs-Ringer-HEPES (KRH) buffer: NaCl: 125, KCl: 5, MgSO$_4$: 1.2, KH$_2$PO$_4$: 1.2, CaCl$_2$2H$_2$O: 2, Glucose: 6, HEPES: 25, pH: 7.4 (pH adjusted with NaOH)

Buffer B (dye loading buffer) KRH buffer with 2.5 µM probenicid: same as buffer A, but probenicid added to final concentration of 2.5 µM. Probenecid (Cat. # P-8761, Sigma Chemical Co., St. Louis, Mo.) made as a stock solution at 250 mM.

Buffer C (dye washout buffer) KRH buffer with 0 mM $K^+$ and 2.5 µM probenicid: NaCl: 130, MgSO$_4$:1.2, NaH$_2$PO$_4$: 1.2, CaCl$_2$2H$_2$O: 2, Glucose: 6, HEPES: 25, pH 7.4 (pH adjusted with NaOH).

Buffer D (compound dilution buffer): Buffer C with 0.1% w/v bovine serum albumin (BSA; Sigma).

D. Pharmacological Standards and Compounds.

The following solutions were used to obtain the data disclosed herein.

Nitrendipine: (RBI Chemicals, Natick, Mass.): Stock: 10 mM in DMSO; Pipetting solution: 9 µM; pipette 20 µL into 120 µL volume in well for final well concentration: 1 µM.

w-Conotoxin MVIIA: (Cat. # H-8210; Bachem Inc., Torrance, Calif.): Stock: 1 mM in HPLC grade $H_2O$ with 0.1% BSA; Pipetting solution: 4.5 µM; pipette 20 µl into 140 µl volume in well for final well concentration: 1 µM.

Test compound stock and solution preparation: Compounds prepared daily as stocks at 10 mM in 100% DMSO; Pipetting solution: 45 µM or serial dilutions thereof; pipette 20 µL into 140 µL volume in well for final well concentration: 1 µM or 10-fold dilutions thereof.

High potassium (depolarization) solution: Buffer C with 240 mM $K^+$ added; pipette 80 µL into 160 µL volume in well for final well concentration of 80 mM $K^+$.

E. Cell Loading with Fluorescent Dyes.

Fluorescent dye solution preparation: A calcium indicator dye, Fluo-4 acetylmethylester (Fluo 4-AM; Cat. # F-124201; Molecular Probes, Eugene, Oreg.) was used to measure changes in intracellular free calcium with FLIPR. 1 mM Fluo-4 AM stock solution was made by dissolution in DMSO. This stock was then diluted to 4.6 µM with Buffer B (Fluo-4 AM working solution).

Cell loading procedure: Plates containing cells were washed with Buffer A using an automated cell washer (Model #: 5161552, Labsystems Oy, Helsinki, Finland) with controls set to the following parameters: cell height: C/D; cell pulse: 4/5, washes: 3; volume: 5; DRY position setting. These settings resulted in a 70 µL residual depth of buffer over cells in each well. 100 µL of the Fluo-4 AM working solution was then added to each well resulting in a final Fluo-4 AM concentration of 2.7 µM Cells were incubated in this solution at 37° C. for 1–1.5 h. Cells were then washed with Buffer C five times using the cell washer with parameters the same as the pre-loading washes above with the exceptions of: washes: 5; WET position setting. A final wash was then conducted by changing the parameters as follows: washes: 1; volume: 2. This resulted in a final well volume of 120 µL. Cells were allowed to equilibrate under this condition for 10 min, and then used in the FLIPR protocol.

F. FLIPR Protocol

Instrumentation: Real time changes in intracellular free calcium in response to potassium-induced depolarization in the absence or presence of putative N-channel inhibitors were measured by either a FLIPR I or FLIPR II (configured for 96-well format) instrument (Molecular Devices, Sunnyvale, Calif.). Identical settings and protocols were used with each instrument, and results obtained from the two instruments were indistinguishable for a set of standard benchmark compounds.

FLIPR hardware settings: Laser power was set to about 0.3 watts. Excitation wavelength was set to a 488 nm peak, and the emission wavelength to 540 nm. Camera aperture was set to 2. All experiments were conducted at room temperature (20–22° C.).

Plate layout—reference signals: Certain wells on each plate were allocated to standards to determine minimum and maximum specific fluorescent signal against which inhibitory effects of compounds were normalized. The reference standards were distributed at plate locations including edge and interior wells Maximum signal (N-channel+non-specific): 12 wells were incubated in nitrendipine (1 µM) solution and 80 mM $K^+$ added to determine maximal $Ca^{2+}$ increase mediated by N-channels+non-specific (non-D-, non-N-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 µM)+w-conotoxin MVIIA and 80 mM $K^+$ added to determine background $Ca^{2+}$ with all N-channels pharmacologically occluded. The peak non-specific signal component was typically less than 15% of the maximum signal peak amplitude.

N-channel reference small molecule: A compound that had been characterized extensively with respect to N-channel inhibitory activity in both FLIPR and patch clamp electrophysiology was included on each plate in triplicate at 1 µM (near $IC_{50}$) to establish a reference point.

Test compounds: 5 test compounds were evaluated for potency on each plate. Each compound was tested at 5 increasing concentrations spanning half-log units and typically reaching a maximal concentration of 10 µM. Each concentration was tested in triplicate wells.

Protocol structure: The FLIPR protocol was configured as three solution addition/sampling sequences (see below). Conotoxin (1 µM final conc.) was added to appropriate wells prior to placing the plate in the FLIPR instrument. Wells initially contained a total solution volume of 100 µl, and after all three solution additions contained 240 µl. The active mixing (by the pipette) option was not used in any sequence.

Nitrendipine addition sequence; 28 s total duration with fluorescence signal sampling at 1 Hz for 2 s, followed by addition of 20 µL nitrendipine standard solution at 10 µL/s, followed by sampling at 0.5 Hz for 24 s.

Test compound addition sequence: 64 s total duration with sampling at 0.5 Hz for 4 sec. test solution addition of 40 µL at 20 µL/s, followed by sampling at 0.2 Hz for 60 s.

Compound incubation, cell depolarization and calcium readout sequence: 1024 s total duration with sampling at 0.0167 Hz for 840 s, followed by solution addition 80 µL of high $K^+$ (depolarization) solution, followed by sampling at 1 Hz for 180 sec. This final 180 sec sampling interval thus represented the epoch where the peak increase in intracellular calcium due to flux through activated N-channels occurred.

G. Data Analysis

FLIPR software: Prior to export, the data was normalized within the FLIPR software module for two effects.

Baseline correction: The baseline was corrected by "zeroing" at sample # 57 (immediately prior to KCl addition). This normalization served to correct the y axis offset of the fluorescent trace from each well so that all traces had a common point just prior to onset of the relevant evoked fluorescence increase.

Spatial uniformity correction factor: The data was normalized by a procedure which calculates a mean over the plate of fluorescent units from the first sample, and then multiplies the data from each well by a scalar that adjusts the value of the first sample to this average value, thus normalizing for differences in absolute baseline fluorescence amongst the wells caused by differences in cell densities or dye loading.

External software: Data were exported from FLIPR into Excel as "*.squ" extension files. Following export, operations were performed in Excel to calculate the maximal peak amplitude (relative to the zeroed baseline) of the fluorescence increase following potassium addition in each well. Measurements from wells where an test compound was added were then normalized as a percentage between the mean amplitudes from the reference wells providing the maximum (100%) and non-specific (0%) signal components, as described above. The resulting percent inhibition by test compounds was considered to reflect inhibition of calcium flux at the N-type channel.

II. L-channel FLIPR Assay.

The methods described below provided a reliable FLIPR-based readout of the efficacy and potency with which test compounds inhibited calcium flux through the L-type calcium channel expressed natively in a human-derived neuroblastoma cell line, SK-N-SH. The degree to which a given compound concentration inhibited the L-channel was determined by comparing the amplitude of peak calcium increase to an 80 mM $K^+$ stimulus in the test well to the peak increase in wells without compound The assay was validated by obtaining 5-point concentration-response curves and thereby determining $IC_{50}$ values for the reference L-channel blockers, nitrendipine (30 mM), nifedipine and verapamil. These values were compatible with the known literature values for these agents to block $Ca^{2+}$ flux through the L-channel.

A. Cell Culture:

An immortalized cell line, SK-N—SH, derived from human neuroblastoma cells (ATCC product # HTB-11) was used for all experiments. Cells were grown in T75 flasks containing Eagle's minimum essential medium (MEM) w/Earle's salts, with 0.1 mM non-essential amino acids, 1.0 mM Na pyruvate and 10% fetal bovine serum (FBS; Cat. # SLM-034-B, Specialty Media). Cells were grown to 100% confluency (by visual microscopic estimation) before sub-culture. Cells were sub-cultured at a ratio of 1:3 by first rinsing with 3 mL PBS, replacing the PBS with PBS containing 0.25% trypsin until the cells detached from the surface. 1 mL of the resulting suspension was then added to a new flask containing 10 mL fresh media. Cells were then incubated (37° C., 5% $CO_2$), and media was exchanged about 3 days after subculturing.

B. Preparation of Cells for Experiments:

Cells used for experiments were at the 100% confluency growth stage. Each flask provided enough cells for three 96-well plates. Cells were detached from the flask by addition of 0.25% trypsin, as described for the sub-culturing protocol. Once detached, 7 mL fresh media was added to the flask, and the solution triturated gently. An additional 20 mL media was then added, and 100 mL of this final cell suspension was then added to each well of a 96-well plate. Before use in experiments the plates were incubated at 37° C. in 5% $CO_2$ until cells reached 100% confluence (1–2 days).

C. Experimental Procedures:

The composition of solutions, hardware settings, plate layout, structure of the FLIPR protocol, and analytical settings and procedures were identical to those described herein for the N-channel assays with the following differences as regards Plate layout and reference signals.

Maximum signal (L-channel+non-specific): 12 wells received 20 μL buffer addition only (no nitrendipine) in the first solution addition sequence to define the maximal $K^+$-evoked $Ca^{2+}$ increase mediated by L-channels+non-specific (non-L-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 μM), followed by 80 mM $K^+$ added to determine background $Ca^{2+}$ with all L-channels pharmacologically occluded. The peak non-specific signal component was typically less than 15% of the maximum signal peak amplitude.

L-channel reference small molecule: Nitrendipine was included in triplicate wells on each plate at 30 nM (near $IC_{50}$) for a reference readout.

III. N-Channel Patch Clamp Electrophysiology.

Conventional whole cell recording techniques were used to directly measure the ability of test compounds to inhibit $Ca^{2+}$ current through N-type calcium channels. N-type current were recorded from both neuronally differentiated IMR-32 cells, and native neurons freshly dissociated from superior cervical ganglia of early postnatal rats. Each day, currents in both cell types were confirmed as N-currents showing that greater than 90% of the total inward current during depolarizing steps was blocked by a supramaximal concentration (3 mM) of w-conotoxin MVIIA. Additionally, the potency of w-conotoxin MVIIA was periodically determined to be about 3 nM ($IC_{50}$), a value consistent with that reported in the literature. Results for a subset of compounds tested in both cell types did not differ significantly, thus data are considered as one data set unless otherwise specified.

A. MR-32 Cell Culture and Differentiation:

IMR32 cells were cultured and neuronally differentiated using procedures identical to those described for the FLIPR N-channel assay except that for differentiation cells were plated in 35 mm plexiglass culture dishes, rather than 96-well plates.

B. Dissociation of Rat Superior Cervical Ganglion (SCG) Neurons:

7–10 day old rat pups were euthanized in a chamber containing a high $CO_2$ atmosphere. Immediately, SCG were surgically isolated, removed and placed in ice cold Hanks balance salt solution (HBSS). SCG's were desheathed, cut open and placed in a solution of HBSS containing 20 U/mL papain (37° C.) for 15 min. The papain solution was then exchanged for HBSS (37° C.) containing 16 mg/mL dispase and 400 U/mL collagenase for 40 min with gentle trituration of tissue every 15 min. Cells were then recovered by centrifugation and stored in L-15 medium at 4° C. for use on the same day. For recording, a drop of cell containing solution was placed on a poly-L-lysine coated 35 mm plexiglass culture dish, and cells allowed to adhere for several minutes.

C. Electrophysiological Procedures:

Solutions: Recording solutions were adapted from those described by Thompson and Wong (1991) *J. Physiol.*, 439: 671–689. Solutions were stored as aliquots for not more than one month (intracellular, −20° C., extracellular, 4° C.) before experiments. The pipette (intracellular) solution contained (in mM): TRIS, 130; CsBAPTA, 10; HEPES, 10; $Mg^{2+}$ ATP, 5; pH to 7.3 with methanesulphonic acid; osmolality ~315 mOsm. Extracellular solution contained (in mM): TRIS 120; CsCl, 5; HEPES, 10; $Mg^{2+}Cl$, 1; $Ba^{2+}Cl$, 5, glucose, 25; tetraethylammonium chloride, 15; tetrodotoxin, 200 (added at time of experiment); pH to 7.4 with methanesulphonic acid; osmolality ~320 mOsm.

Whole cell recording and analysis: The whole-cell voltage clamp configuration of the patch clamp technique as described by Hamill et al. (1981) *Pflügers Arch.* 391: 85–100, was employed to isolate voltage-dependent calcium currents. Culture dishes containing cells were placed in a chamber on the stage of an inverted microscope. All experiments were conducted at room temperature (20–22° C.). Patch pipettes were fabricated from thin-wall glass (1.5 mm OD, 1.12 mm ID; World Precision Instruments, New Haven, Conn.) on the Brown-Flaming P-86 puller (DC resistance: 3–6 MΩ; Sutter Instr. Co., Novato, Calif.). An Axopatch 1B amplifier (Axon Instruments, Foster City, Calif.) was used to obtain current signals and this was connected to a personal computer by either a TL-1 (Scientific Solutions, Solon, Ohio.) or Digidata 1200 (Axon Instr.) interface. The current signal was balanced to zero with the pipette immersed in the bath just prior to forming a seal on the neuron. Seal resistance ranged from 1 to greater than 10 GΩ. Series resistance was usually less than 10 MΩ, and was not compensated electronically. Digitized data acquisition and voltage step protocols were accomplished with pClamp 6.0 software (Axon Instr). Data were low-pass filtered at less than one-half the digital sampling rate prior to digitizing. To record N-type currents for evaluation of inhibitory potency of compounds (steady-state concentration-response analysis), 200 ms voltage steps to +10 mV were delivered at 15 sec intervals from a holding potential of −90 mV. The recorded currents were leak subtracted on-line with a PA or P-6 subpulse protocol in the pClamp software. To evaluate open channel block of compounds, 10 ms voltage steps to +10 mV were delivered at varying frequencies from a holding potential of −90 mV without using on-line leak subtraction. These voltage protocols both yielded constant inward current amplitudes over 5–10 minutes of recording. Peak current amplitude was analyzed using the clampfit module of pClamp software. Origin 5.0 software (Microcal Corp, Northampton, Mass.) was used to iteratively fit concentration-response data to a standard Hill function, and to provide graphic displays for current traces and analyzed data.

Drug/compound preparation and delivery: Test compounds were prepared as 10 mM stock solutions in DMSO, and appropriate volumes of these stock solutions dissolved into extracellular buffer to yield the desired concentrations. Solutions containing drugs/compounds were applied focally from any of six linearly arranged glass-lined tubes (200 mm o.d., Hewlett Packard, Wilmington, Del.) positioned 100 mm from the recorded neuron. Each solution was released from the desired tube by an electronically controlled solenoid valve system (BME Systems, Baltimore, Md.). This system achieved rapid (<100 ms) equilibration of drug solution in the extracellular phase without perturbing the recording characteristics.

Compounds of the invention generally had a binding affinity, expressed as the $IC_{50}$ (μM), for the N-type calcium channel, as measured by the FLIPR assay, of about 10 μM of less. Table 1 shows the results for certain compounds of the invention.

TABLE 1

| Example No. | $IC_{50}$ (μM) |
| --- | --- |
| 1 | 36.28 |
| 3 | 17.23 |
| 4 | 3.54 |
| 5 | 5.83 |
| 6 | 6.11 |
| 7 | 1.99 |
| 9 | 2.71 |
| 10 | 3.81 |
| 11 | 6.91 |
| 12 | 1.89 |
| 13 | 10.48 |
| 14 | 2.59 |
| 15 | 4.13 |
| 16 | 81.58 |
| 19 | 7.96 |
| 20 | 3.18 |
| 21 | 2.54 |
| 23 | 3.51 |
| 24 | 2.68 |
| 25 | 4.83 |
| 26 | 4.90 |
| 27 | 5.55 |
| 28 | 3.81 |
| 29 | 5.44 |
| 32 | 6.46 |
| 33 | 2.82 |
| 33 | 2.82 |
| 37 | 2.18 |
| 38 | 9.15 |
| 39 | 4.53 |
| 40 | 2.98 |
| 41 | 1.80 |
| 44 | 5.39 |
| 48 | 7.74 |
| 49 | 5.88 |
| 50 | 5.90 |
| 51 | 3.78 |
| 53 | 7.19 |
| 54 | 1.75 |
| 55 | 2.31 |
| 56 | 6.38 |

IV. Formalin Test

The Formalin test assesses the inhibitory effects of orally administered N-type calcium channel antagonist on formalin-induced nocifensive behaviours in rats. The formalin test is a well established pain test (Dubuisson and Dennis, 1977; Wheeler-Aceto et al., 1990; Coderre et al., 1993). This consists of two distinct phases of formalin-induced behaviour. The first phase response, occurring between 0 to 5 minutes, is caused by acute nociception to the noxious chemical (formalin) injected into the paw. This is followed by a quiescent period of between 5 to 15 min post injection. A second phase response, occurring after 15 minutes and lasting up to 60 minutes, is caused by sensitisation of the central neurons in the dorsal horn. Central sensitisation augments the noxious afferent input and a stronger pain barrage is transmitted into the brain. Inhibition of the second phase response is indicative of a central mechanism of drug action.

The procedure for the formalin test is as follows: male rats are placed in a plexiglass chamber and observed for 30–45 min. to observe their baseline activity. Multiple groups of animals are pretreated with either vehicle or different doses of a test compound. Animals are dosed with the drug of interest either 40 min., if by the intraperitoneal route, or 90 min., if by the oral route, prior to injection of formalin into a hind paw (under the dorsal skin; 0.05 mL of sterile 5% formalin). The number of paw flinches and licks during first phase (0–5 min.) and second phase (20–35 min.) are scored and recorded. Flinch and lick responses are calculated as percentage of inhibition compared with the mean score of a saline control group. Drug potencies are expressed as the dose which causes 50% of the maximum inhibitory effect ("$ID_{50}$"). Student t-tests are used for statistical analysis to determine the significance of drug effects. Compounds are considered active based on their ability to inhibit the flinch response.

V. Chronic Constrictive Injury Test.

The Chronic Constrictive Injury ("CCI") test or Neuropathic Pain Model assesses neuropathic pain associated with nerve injuries that can arise directly from trauma and compression, or indirectly from diseases ranging from infection to cancer, metabolic conditions, toxins, nutritional deficiencies, immunological dysfunction and musculoskeletal changes. In the CCI model (Bennett and Xie, 1988) a unilateral peripheral neuropathy is produced in rats by partial nerve ligation.

Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifurcation, is exposed and ligated 4 times with chromic gut suture. The suture is tied with about 1 mm spacing between ligatures. The incision is closed in layers and the animals are allowed to recover. Thermal hyperalgesia is measured using the paw-withdrawal test (Hargreaves et al, 1988). Nerve compression due to the partial nerve ligation causes shorter latencies for paw withdrawal compared to the latency of paw withdrawal of paws of normal or sham operated legs. Animals are habituated on an elevated glass floor. A radiant heat source is aimed at the mid-plantar hindpaw (sciatic nerve territory) through the glass floor with a 20 second cut-off used to prevent injury to the skin. Latencies for the withdrawal reflex in both paws are recorded. Response to test compounds are evaluated at different times following oral administration to determine onset and duration of drug effect. Dose response studies are conducted with multiple groups of CCI rats dosed orally with either vehicle or the test compound for 5 days. Paw withdrawal latencies are measured each day prior to the first daily dose. Data analysis is performed by multiple means comparison (Dunnett's test) and drug potencies are expressed as the dose which causes 50% of the maximum efficacy ("$EC_{50}$").

Chemical Methods:

Method A:

Exemplary compound 19, 2-(4-cyclohexylphenyl)-quinoline-4,6-diamine, see Table 1 hereafter, was made by the following method. Other compounds prepared by Method A from suitable precursors are listed in Table 1.

A1. 3-(4-Cyclohexylphenyl)-3-oxo-propionic acid ethyl ester:

Into a three-neck 2 L round-bottom flask equipped with an addition funnel, nitrogen inlet, magnetic stirrer, heating mantle, thermocouple and condenser, was placed 21.7 g (0.543 moles) of a 60%-in-oil dispersion of sodium hydride. To this was added dry hexane (1 L). The resulting suspension was stirred for 15 minutes, stirring was halted and the solids were allowed to settle. The clear supernatant containing the hexane and dissolved oil was then removed via a cannula. Diethyl carbonate (1 L) was added and the suspension was heated to 120° C. To this suspension was cautiously added dropwise, over 40 minutes, a solution of 100 g (0.494 moles) of 4'-cyclohexyl acetophenone dissolved in 250 mL of diethyl carbonate. As addition proceeded a reaction initiated, hydrogen was evolved and the color changed to tan. After the acetophenone derivative addition was complete, the reaction was heated for 1 additional hour. The reaction mixture was cooled and was poured into a 2 L separatory funnel. The diethyl carbonate layer was twice washed with 10% acetic acid solution and then dried over $MgSO_4$. The solution was then filtered and concentrated on a rotary evaporator followed by pumping with high vacuum at 70° C. for 18 hr. The concentrated solution crystallised on cooling over 24 hrs to give a colorless solid. The product obtained was then used without further purification, yield 133 g (98%). 1H NMR reveals that the β-keto ester product actually exists as a keto-enol tautomer mixture in solution, with the keto form predominant in the solid.

A2. 3-(4-Acetylamino-phenylamino)-3-(4-cyclohexylphenyl)-acrylic acid butyl ester:

Into a 1 liter single-neck round-bottom flask equipped with a Soxhlet extractor apparatus with condenser, magnetic stirrer and nitrogen inlet was placed 50.25 g (0.183 moles) of 3-(4-cyclohexylphenyl)-3-oxo-propionic acid ethyl ester, 25 g (0.167 moles) of 4'-aminoacetanilide, 1.55 g (0.008 moles) 4'-aminoacetanilide hydrochloride salt and 500 mL of dry n-butanol. Into the Soxhlet thimble (33×118 mm) was placed highly activated 4A sieves (1.7–2.4 mm beads). These sieves are activated immediately before use under high vacuum with heating (400° C. for 30 min). The mixture was then brought to reflux such that the butanol azeotropically removed water, driving the equilibrium reaction, and the water was removed from the butanol by the sieves before being returned to the reaction pot. The reaction was allowed to continue for 48 hrs. It was necessary to replace the charge of sieves after the first 24 hrs. Transesterification to the butyl ester along with removal of ethanol occurs concomitantly with enamine formation. After 48 hrs the reaction pot was cooled, then placed in a –40° C. freezer and crystals were allowed to form over 24 hrs. The crystals were collected by vacuum filtration and the solids washed with cold ethanol. The product was then dried in a vacuum oven to give 73.8 g (98%) of the desired enamine.

A3. N-[2-(4-Cyclohexylphenyl)-4-hydroxy-quinolin-6-yl]-acetamide:

Into a 2 L three-neck round-bottom flask equipped with a condenser, magnetic stirrer, thermocouple, heating mantle with a variable voltage controller, and a nitrogen inlet, was charged 1.2 L of Dowtherm A (a eutectic mixture of 26.5% diphenyl and 73.5% diphenyl oxide). The Dowtherm A was then preheated to 250° C. To this was cautiously added in small portions 48 g (0.11 moles) of 3-(4-acetylamino-phenylamino)-3-(4-cyclohexylphenyl)acrylic acid butyl ester. As portions were added gas was evolved and foaming occurred. Crystals of product begin to form and adhere to the sides. After all the material had been added the heating of the reaction was continued for 1 hour. The mixture was then cooled to room temperature and hexane was added. The solid product was collected by vacuum filtration and washed with hexane. After drying in a vacuum oven, 35.7 g (90%) of product was recovered.

A4. N-[2-(4-Cyclohexylphenyl)-4-methoxy-quinolin-6-yl]-acetamide:

Into a 500 mL three-neck round-bottom flask equipped with a condenser, magnetic stirrer and nitrogen inlet was added 35.7 g (0.099 moles) of N-[2-(4-cyclohexylphenyl)-4-hydroxy-quinolin-6-yl]-acetamide. The material was suspended in 250 mL of toluene with stirring and then 20.6 mL (0.21 moles) of dimethyl sulfate was added. The resulting suspension was heated with a silicone oil heating bath, to gentle a reflux for 18 hr. After this time the reaction was allowed to cool and hexane was added. The solids were collected by vacuum filtration and washed with hexane.

After drying, the solids were suspended in a 2 L Erlenmeyer flask with 1 L of 5% sodium hydroxide solution. The vigorously stirred suspension was then heated to 70° C. for 30 min. This step converted the salt form of the material to the free base and removed some impurities. After cooling the solids were collected by vacuum filtration and then washed with water. The product was dried in a vacuum oven to give 35.8 g (96%) of a material which contained approximately 30% of side products, with the N-methylated material constituting the major impurity. This material was used in the following procedure without further purification.

A5. N-[4-Amino-2-(4-cyclohexylphenyl)-quinolin-6-yl]-acetamide:

Into a 500 mL three-neck round-bottom flask equipped with a mechanical stirrer and condenser, nitrogen inlet and gas outlet was placed 35 g of N-[2-(4-cyclohexylphenyl)-4-methoxy-quinolin-6-yl]-acetamide and 250 g of ammonium acetate. The stirred solid suspension was then brought to up to 115° C. Ammonia evolution began, and the material slowly fused and dissolved in the acetic acid that formed over time. The temperature was slowly raised to 140° C. over 1 hr. Caution was used to ensure that the condenser and gas outlet remained clear of solid ammonium acetate, which can collect on cool surfaces from sublimation of excess ammonium acetate. After 4 hours of heating, the reaction was cooled and poured into 1 L of water. The pH was then adjusted to 9.5 by the slow addition of concentrated a NaOH solution with application of ice cooling. Ethyl acetate was then added and the mixture was filtered. Solid impurities, some of which are due to N-methylated side products from the previous step, are removed and the liquid filtrate was poured into a 2 L separatory funnel. The ethyl acetate layer was separated, washed twice with 5% NaOH solution and then dried over $Na_2SO_4$. After filtration, the solvent was evaporated to give 22 g (60%) of a solid which mostly consisted of the product and about 20% of the 6-N-deacetylated material, 2-(4-cyclohexylphenyl)-4,6-quinolinediamine. This product was then used without further purification in the following acetate-removal step.

A6. 2-(4-Cyclohexylphenyl)-4,6-quinolinediamine:

The 22 g of material from the previous step was placed in a 1 L flask to which 500 mL of 6 N HCl was added. The mixture was then heated with stirring to 95° C. for 18 hrs. After this time, the solution was cooled in ice and was then cautiously neutralised with concentrated NaOH solution, followed by adjustment to pH 9.5. The solution was then poured into a 2 L separatory funnel and extracted with ethyl acetate. The organic layer was then dried over $Na_2SO_4$, filtered and concentrated to give 17 g of product. Repeated crystallisation using methanol, methylene chloride and hexane gave 9.0 g (41%) of the diamino quinoline product.

A7: 3-(Methyl-phenoxy)-3-oxo-propionic acid ethyl ester:

3-(Methyl-phenoxy)-3-oxo-propionic acid ethyl ester used for the preparation of the compound of Example 14, was prepared as follows. In a 12 L round bottom flask equipped with mechanical stirrer, thermometer, addition funnel and nitrogen inlet was placed 160.0 grams (60%, 4.0 moles) of sodium hydride dispersion in mineral oil. The flask was cooled with an ice bath and 3.5 L of dry THF added with stirring, while maintaining the temperature below 20° C. To the suspension of stirred sodium hydride was added 376.4 grams (4.0 moles) of phenol dissolved in 0.3 L of THF. The addition was carried out at such a rate so as to maintain the temperature below 10° C. over the course of approximately 2 hours. The mixture was then allowed to warm to room temperature and stir for 1 hour. To the re-cooled solution, over the course of 1 hour, was added 418 grams (2.0 moles) of ethyl 4-bromoacetoacetate (A. Svendsen and P. M. Boll, *Tetrahedron* 1973 29, 4251–4258) dissolved in 0.3 L of THF. The rate of addition was controlled so as to maintain the temperature below 10° C. The ice bath was removed and the brown slurry stirred overnight at room temperature. The reaction was quenched by pouring into 2.2 L of 1.0 N hydrochloric acid and the phases separated. The aqueous phase was extracted with 0.5 L of diethyl ether; the combined organic phase washed with 1.0 L of saturated brine and dried over $MgSO_4$. After filtering and removal of solvent a red-brown oil was obtained, 830 gram of crude product. The crude product was dissolved in 0.4 L of hexane and applied to a column of 8.0 L of silica wet-packed in hexane. The column was eluted with 4.0 L of hexane; 8.0 L of 3:1 hexane to diethyl ether and 12.0 L of 2:1 hexane to diethyl ether. The second fraction, 459.3 gram, was reapplied to a column of 4.0 L of silica wet-packed in hexane. The column was eluted with 3.0 L of 95:5 hexane to diethyl ether; 2.0 L of 9:1 hexane to diethyl ether; 2.0 L of 4:1 hexane to diethyl ether and 12.0 L of 3:1 hexane to diethyl ether. The major fraction was bulb-to-bulb distilled using a Kugelrohr apparatus and an oven temperature of 40–45° C. at <1.0 torr. The desired product was obtained as an oil, 145.9 gram (33%).

Method B:

Exemplary compound 10, 2-(3-fluorophenyl)-quinoline-4,6-diamine, see Table 1 hereafter, was made by the following method. Other compounds prepared by Method B from suitable precursors are listed in Table 1.

B1. 3-(3-Fluorophenyl)-3-oxo-propionic acid ethyl ester:

The title compound was prepared from m-fluoro acetophenone, by a method analogous to the preparation of 3-(4-cyclohexylphenyl)-3-oxo-propionic acid ethyl ester in step A1 of Method A, except that the product was purified by vacuum distillation (bp 114–117° C. at 0.8–0.9 mm Hg) in 91% yield.

B2. 3-(4-Nitro-phenylamino)-3-(3-fluorophenyl)-acrylic acid butyl ester:

Into a dry 2 L round-bottom flask was placed 106.3 grams (0.506 moles) of 3-(3-fluorophenyl)-3-oxo-propionic acid ethyl ester, 63.0 grams (0.456 moles) of 4-nitro-aniline and 4.0 grams (0.023 moles) of 4-nitro-aniline hydrochloride. To the mixture was added 1.3 L of n-butanol, the flask was fitted with a Soxhlet extractor (cup volume of 0.3 L), condenser and nitrogen inlet. Dry, activated 4 Å sieves (200 grams) were placed in the extractor cup and the reaction mixture heated to reflux temperature of 118° C. under nitrogen and maintained at that temperature for 90 hours. The reaction mixture was decanted while hot from a small amount of solids and chilled to −15° C. for 48 hours Crystalline solids were collected by vacuum filtration. The crystals were washed with 0.2 L of cold ethanol and two 0.2 L portions of hexanes and vacuum dried at 50° C. overnight to yield 35.8 grams (20.8% yield) of the title compound.

The mother liquors were concentrated, diluted with 1.0 L of toluene and the toluene removed in vacuo; this process was repeated two times. The liquors were then diluted in 1.0 L of n-butanol and another 1.75 grams (10.0 mmol) of 4-nitro-aniline hydrochloride added; the flask was fitted with a soxhlet extractor as before and the cup charged with a fresh 200 grams of sieves. The mixture was placed under nitrogen and brought to reflux temperature for 90 hours. The reaction was cooled and then reduced to a final volume of 0.6 L in vacuo. The solution was then seeded with crystalline 3-(4-nitro-phenylamino)-3-(3-fluorophenyl)-acrylic acid butyl ester and let stand at −15° C. for 48 hours. The crystals were collected as before; 64.3 grams obtained after drying. Analysis showed this material to be contaminated with 4 nitroaniline and it was purified by flash chromatography. The product was dissolved in 0.5 L of 1:1 methylene chloride to hexane and applied to a column of 3.0 L of silica wet-packed in 1:1 methylene chloride to hexane. The column was eluted with 4.0 L of 1:1 methylene chloride to hexane; 9.0 L of 2:1 methylene chloride to hexane; and 2.0 L of methylene chloride. Fractions of 0.5 L were collected and those containing the desired product combined to yield 41.7 grams (24.3%) of bright yellow solid. The combined yield was 45.1%.

B3. 2-(3-Fluorophenyl)-6-nitro-quinolin-4-ol:

In a 3 L three-neck flask, equipped with mechanical stirrer, Claisen adapter holding a thermocouple probe and reflux condenser with nitrogen inlet was added 0.75 L of Dowtherm A (a eutectic mixture of 26.5% diphenyl and 73.5% diphenyl oxide) The solvent is then preheated to 250° C. To this was cautiously added in small portions 77.0 grams (0.215 moles) of 3-(4-nitro-phenylamino)-3-(3-fluorophenyl)acrylic acid butyl ester over the course of 0.25 hours. The mixture was maintained at 250° C. for 1.5 hours and then allowed to cool to 90° C. over the course of 2 hours. The mixture was treated with 1.0 L of hexanes, and allowed to cool to room temperature while stirring overnight. The tan solids were collected by suction filtration and washed with three 0.15 L portions of hexanes. The solids were dried under vacuum at 50° C. overnight to yield 58.63 grams (96.0%) of the title compound.

B4. 6-Bromo-4-chloro-2-(3-fluorophenyl)-quinoline:

Into a 500 mL three-neck round-bottom flask equipped with a condenser, magnetic stirrer and nitrogen inlet was placed 5.2 g (16.3 mmoles) of 6-bromo-2-(3-fluorophenyl)-quinolin-4-ol. To this was added 15.2 mL (25.0 g, 163 mmoles, 10 equiv.) of phosphorus oxychloride with stirring. The mixture was then heated to 110° C. for 4 hr. At the end of this time the reaction was cooled to room temperature and water cautiously added dropwise until all of the $POCl_3$ was consumed. The product crystallised from the water and the solids were collected by filtration. The solids were washed with water and placed in a 250 mL Erlenmeyer where they were then triturated with water. After collection by filtration, washing with water, and drying in a vacuum oven, 4.6 g (84%) of the pure product was obtained.

B5. 6-Bromo-4-azido-2-(3-fluorophenyl)-quinoline:

Into a 250 mL three-neck round-bottom flask equipped with a condenser, magnetic stirrer, silicone oil heating bath, nitrogen inlet and gas outlet was placed 3.2 g (9.50 mmoles) of 6-bromo-4-chloro-2-(3-fluorophenyl)-quinoline. To this was added 75 mL of N-methyl pyrrolidinone then 6.0 g (95 mmoles, 10 equiv.) of sodium azide. The stirring mixture was then warmed to 60° C. for 18 hr. At the end of this time the reaction was cooled, then poured into a 1 L separatory funnel containing 500 mL water and 250 mL of ethyl acetate. The pH was adjusted to 9.0 the layers were separated. The aqueous layer was then extracted twice with 100 mL of ethyl acetate. The organic layers were combined, dried over $Na_2SO_4$, filtered and concentrated to give a product, which was carried to the next step without further purification.

B6. 4-Azido-2-(3-fluorophenyl-6-nitro-quinoline:

The title compound was prepared by a procedure analogous to that of step B5 for 6-bromo-4-azido-2-(3-fluorophenyl)-quinoline. The product was isolated on a 16.16 mmole scale.

B7. 2-(3-Fluorophenyl)-4,6-quinolinediamine:

Into a 500 mL three-neck flask equipped with a condenser, magnetic stirrer, nitrogen inlet gas outlet and a silicone oil heating bath was placed 4-azido-2-(3-fluorophenyl)-6-nitro-quinoline. The material was suspended in 250 mL of ethyl acetate and 50 mL of ethanol. The stirred mixture was heated to reflux, then 20 g (89 mmoles, 6 equiv.) of stannous chloride dihydrate was cautiously added portionwise over 40 min. The reaction was then heated for an additional 2 hr. At the end of this time, the reaction was cooled and then poured into 500 mL of water. The pH was cautiously adjusted to 9.0 and the solution filtered. The solids were washed with 100 mL of ethyl acetate, the filtrates combined and the aqueous layer extracted twice with 200 mL of ethyl acetate. The organic layers were combined, dried over $Na_2SO_4$, filtered and concentrated. The product was chromatographed on a silica gel column, using 10% methanol in ethyl acetate as eluent, and was then recrystallised from methylene chloride and hexane to give 3.6 g (88%) of the product.

Method C:

Exemplary compound 29, N6-cyclopropyl-2-(3-fluorophenyl)-N4,N4-dimethyl-quinoline-4,6-diamine, see Table 1 hereafter, was made by the following method. Other compounds prepared by Method C from suitable precursors are listed in Table 1.

C1. 3-(3-Fluorophenyl)-3-oxo-propionic acid ethyl ester:

Preparation of the title compound is described in step B1 of Method B.

C2. 3-(4-Bromo-phenylamino)-3-(3-fluorophenyl)-acrylic acid butyl ester:

The title compound was prepared in 86% yield by a procedure analogous to the preparation of 3-(4-acetylamino-phenylamino)-3-(4-cyclohexylphenyl)-acrylic acid butyl ester, step A2 of Method A.

C3. 6-Bromo-2-(3-fluorophenyl)-quinolin-4-ol:

The title compound was prepared in a 92% yield by a procedure analogous to the preparation of 2-(3-fluorophenyl)-6-nitro-quinolin-4-ol, step B3 of Method B.

C4. 6-Bromo-4-chloro-2-(3-fluorophenyl)-quinoline:

Into a 500 mL three-neck round-bottom flask equipped with a condenser, magnetic, stirrer and nitrogen inlet was placed 5.2 g (16.3 mmoles) of 6-bromo-2-(3-fluorophenyl)-quinolin-4-ol. To this was added 15.2 mL (25.0 g, 163 mmoles, 10 equiv.) of phosphorus oxychloride with stirring. The mixture was heated to 110° C. for 4 hr. At the end of this time the reaction was cooled to room temperature and water was cautiously added dropwise until all of the $POCl_3$ was consumed. The product crystallised from the water and solids were collected by filtration. The solids were washed with-water, placed in a 250 mL Erlenmeyer and triturated with water. After collection by filtration, washing with water, and drying in a vacuum oven, 4.6 g (84%) of the product was obtained.

C5(a). N-[6-bromo-2-(3-fluorophenyl)-4-quinolinyl]-N4,N4-dimethylamine:

Into a 500 mL three-neck round-bottom flask equipped with magnetic stirrer, nitrogen inlet, gas outlet, condenser and heating bath was placed 20 g (59.4 mmoles of 6-bromo-4-chloro-2-(3-fluorophenyl)-quinoline. The material was dissolved in 150 mL of N-methyl pyrrolidinone and 250 mL of a 40% aq. solution of dimethylamine was added to the stirring mixture. The reaction was then warmed to 60° C. for 48 hrs. At the end of this time the reaction was cooled, into 3 L of water in a 4 L Erlenmeyer flask and the mixture was stirred until solids formed. The solids were collected by vacuum filtration and dried in a vacuum oven. The product was recrystallised from ethanol in a −20° C. freezer to give 19.6 g (95%) yield of the aminated product.

C5(b). Alternative Procedure:

N-[6-bromo-2-(3-fluorophenyl)-4-quinolinyl]-N4,N4-dimethylamine was alternatively prepared as follows. Into a 1 L Parr bomb equipped with mechanical stirring, thermocouple, heater with controller and pressure gauge was placed 20 g (59.4 mmoles of 6-bromo-4-chloro-2-(3-fluorophenyl)-quinoline. To this was added 350 mL of ethanol and 350 mL of a 40% aq. solution of dimethylamine. The bomb was sealed and the stirred mixture was then heated to 100° C. resulting in a pressure of approximately 150 psi. Heating was continued for 24 hrs. At the end of this time the reaction was allowed to cool to room temperature and was then vented. The contents were then poured into 3 L of water in a 4 L Erlenmeyer flask and the mixture was stirred until solids formed. The solids were collected by vacuum filtration and then dried in a vacuum oven. The crude product was recrystallised from ethanol in a −20° C. freezer to give 18.15 g (92%) yield of the aminated product.

C6. N6-Cyclopropyl-2-(3-fluorophenyl)-N4,N4-dimethyl-quinoline-4,6-diamine:

The title compound was prepared in a fashion analogous to the preparation of N6-cyclopropyl-2-(3-chlorophenyl)-N4,N4-dimethyl-quinoline-4,6-diamine (Method D2).

Method D:

Exemplary compound 55, N6-cyclopropyl-N4,N4-dimethyl-2-(3-morpholin-4-yl-phenyl)-quinoline-4,6-diamine, see Table 1 hereafter, was made by the following method. Other compounds prepared by Method D from suitable precursors are listed in Table 1.

D1. N-[6-Bromo-2-(3-chlorophenyl)-4-quinolinyl]-N4,N4-dimethylamine:

The title compound was prepared in a manner analogous to the procedure of step C5a or C5b of Method C.

D2. 2-(3-Chlorophenyl)-N-6-cyclopropyl-N4,N4-dimethyl-quinoline-4,6-diamine:

The title compound, Example 53, see Table 1 hereafter, was prepared by selective Pd catalyzed substitution of a 6-bromo moiety in the presence of a m-chloro substituent, as follows.

Into each of two 4 dram vials equipped with a magnetic stir bar and a teflon lined septum closure, was placed 1.18 g (3.27 mmoles, 1 equiv.) of N-[6-bromo-2-(3-chlorophenyl)-4-quinolinyl]-N,N-dimethylamine, 73 mg of tris(dibenzylideneacetone) dipalladium(0) (0.08 mmoles, 0.025 equiv., 0.05 equiv. Pd), 397 mg of racemic 2,2'-bis(diphenylphosphino)-1,1'-bisnaphthyl (0.64 mmoles, 0.2 equiv.), 943 mg of sodium tert-butoxide (9.81 mmoles, 3 equiv.) and, finally, 10 mL of THF and of 2 mL of cyclopropylamine (28.9 mmoles, 8.8 equiv.). The vial was placed under a nitrogen atmosphere, sealed and then heated to 70° C. in an oil bath for 18 hr. At the end of this time the reaction vials were cooled, combined, and poured into a 1 L separatory funnel containing 300 mL of ethyl acetate and 500 mL of 1 N NaOH solution. The layers were separated and the organic layer was washed again with 500 mL of 1 N NaOH solution. The organic layers were then dried over $Na_2SO_4$, filtered and concentrated. The residue was then purified by flash chromatography using 5% ethyl acetate in methylene chloride containing 0.5% triethylamine. Fractions containing the desired compound were then combined. The combined fractions were concentrated and the resulting residue crystallised with methylene chloride and hexane to give 1.22 g (55%) of pure product. A later fraction containing 273 mg (14% yield) was also recovered, which corresponded to the decyclopropylated material, N-[2-(3-chlorophenyl)-6-amino-4-quinolinyl]-N-dimethylamine.

D3. N6-Cyclopropyl-N4,N4-dimethyl-2-[3-(4-morpholinyl)phenyl]-4,6-quinolinediamine:

The title compound was prepared by Pd catalyzed substitution of a m-chloro moiety. Into each of two 4-dram vials equipped with a magnetic stir bar and a teflon-lined septum closure, was placed 1.18 g (3.27 mmoles, 1 equiv.) of N-[6-cyclopropyl-2-(3-chlorophenyl)4-quinolinyl]-N,N-dimethylamine, 73 mg of tris(dibenzylideneacetone) dipalladium(0) (0.08 mmoles, 0.025 equiv., 0.05 equiv. Pd), 148 mg of 2-(di-t-butylphosphino)biphenyl (0.49 mmoles, 0.15 equiv.), 943 mg of sodium tert-butoxide (9.81 mmoles, 3 equiv.) and, finally, 10 mL of THF and of 1 mL of morpholine (11.46 mmoles, 3.5 equiv.). The vial was placed under a nitrogen atmosphere, sealed and then heated to 70° C. in an oil bath for 18 hr. At the end of this time the reaction vials are cooled, combined, and poured into a 1 L separatory funnel containing 300 mL of ethyl acetate and 500 mL of 1 N NaOH solution. The layers are separated and the organic layer was washed again with 500 mL of 1 N NaOH solution. The organic layers are then dried over $Na_2SO_4$, filtered and concentrated. The residue was then purified by flash chromatography using 40% ethyl acetate in methylene chloride containing 0.5% triethylamine. Fractions containing the desired compound were then combined. Fractions were concentrated and the resulting residue crystallised with methylene chloride and hexane to give 1.51 g (59%) of product.

Method E:

Exemplary compound 56, 2-(3-morpholin-4-yl-phenyl)-N4,N4-dimethyl-quinoline-4,6-diamine, see Table 1 hereafter, was made by the following method. Other compounds prepared by Method E from suitable precursors are listed in Table 1.

E1. N6-Cyclopropyl-N4,N4-dimethyl-2-[3-(4-morpholinyl)phenyl]-4,6-quinolinediamine:

The title compound was prepared according to the procedure of step D3 of Method D.

E2. N4N4-Dimethyl-2-[3-(4-morpholinyl)phenyl]-4,6-quinolinediamine:

The title compound was prepared by acid catalyzed removal of a cyclopropyl group, as follows. Into a 100 mL round-bottom flask equipped with a condenser, magnetic stirrer, nitrogen inlet and silicone oil heating bath, was placed 600 mg of N6-cyclopropyl-N4,N4-dimethyl-2-[3-(4-morpholinyl)phenyl]-4,6-quinolinediamine. To this was added 30 mL of tetrahydrofuran, 15 mL of water and then 30 mL of conc. HCl solution. The mixture was heated to 65° C. for 3 days. At the end of this time the starting material had disappeared as determined by TLC. The reaction was then cooled, the pH adjusted to 9.0 with sodium hydroxide solution and poured into a 1 L separatory funnel, where it was extracted with 300 mL of ethyl acetate. The organic layer washed with 1 N NaOH, dried over $Na_2SO_4$, filtered and concentrated. The residue was subjected to flash chromatography using 5% methanol in a 50:50 ethyl acetate and methylene chloride mixture containing 0.5% triethylamine to give 305 mg (57%) of the product.

Method F:

Exemplary compound 91, 2-(3-fluorophenyl)-N4,N4-dimethyl-N-6-cyclopropyl-N6-acetyl-quinoline-4,6-diamine, see Table 1 hereafter, was made by the following method. Other compounds prepared by Method F from suitable precursors are listed in Table 1.

F1. N6-Cyclopropyl-N4,N4-dimethyl-2-[3-(4-morpholinyl)phenyl]-4,6-quinolinediamine:

The title compound was prepared according to the procedure of step D3 of Method D.

F2. N-Cyclopropyl-N-[4-(dimethylamino)-2-(3-fluorophenyl)-6-quinolinyl]acetamide:

The title compound was prepared by acetylation at the 6-nitrogen as follows. Into a 50 mL round-bottom flask equipped with a magnetic stirrer, condenser silicone oil bath and nitrogen inlet, was placed 750 mg (2.33 mmoles) of N6-cyclopropyl-N4,N4-dimethyl-2-[3-fluorophenyl]-4,6-quinolinediamine. To this was added 5 mL of glacial acetic acid. After the material dissolved, 202 mg (2.57 mmoles, 1.1 equiv.) of acetyl chloride was added. The mixture was stirred at room temperature for 1 hr, then heated to 60° C. for 2 hr. At the end of this time the reaction was cooled and poured into a 1 L separatory funnel containing 300 mL ethyl acetate and 500 mL of 1 N NaOH solution. The organic layer was separated, washed with NaOH solution, dried over $Na_2SO_4$, filtered and concentrated. The residue was then crystallised from methylene chloride and hexane to give 550 mg (65%) of product.

Method G:

Exemplary compound 18, 2-(3-methoxyphenyl)-N-6-methyl-quinoline-4,6-diamine, see Table 1 hereafter, was made by the following method. Other compounds prepared by Method G from suitable precursors are listed in Table 1.

G1. 2-(3-methoxyphenyl)-4,6-quinolinediamine:

The title compound was prepared in a manner analogous to the procedure of Method A.

G2. N-[4-Amino-2-(3-methoxyphenyl)-quinolin-6-yl]-formamide:

Formic anhydride was prepared by placing 260 mg (5.66 mmoles) of formic acid into a dry 100 mL round-bottom flask equipped with a condenser, magnetic stirrer and a nitrogen inlet. The flask was cooled with an ice bath and then 470 mg (4.61 mmoles) of acetic anhydride was added. The stirring solution was then gently warmed to 50° C. with an oil bath for 2 hrs. After this time the reaction was cooled, and 25 mL of dry THF was added followed by the addition of 1.0 g (3.77 mmoles) of 2-(3-methoxyphenyl)-4,6-quinolinediamine as a solution in 10 mL of dry THF. The mixture was then heated to reflux for 2 hrs. At the end of this time the reaction was cooled and ether was added. The solids which formed were then collected by filtration and washed with ether. The solids were then dissolved in ethyl acetate and 5% NaOH solution, the layers separated and the organic layer dried over $Na_2SO_4$, filtered and concentrated to give 830 mg (75%) of the desired product. This product was used without further purification.

G3. 2-(3-Methoxyphenyl)-N-6-methyl-4,6-quinolinediamine:

Into a 200 mL round-bottom flask equipped with a condenser, magnetic stirrer and nitrogen inlet, was placed 830 mg (2.83 mmoles) of N-[4-amino-2-(3-methoxyphenyl)-quinolin-6-yl]-formamide. To this was added 40 mL of dry THF followed by the cautious addition of 40 mL of a 1.0 Molar solution of Borane THF complex. The solution was then heated to reflux for 18 hrs. At the end of this time the reaction was cooled in ice and then cautiously quenched by the slow addition of 10 mL dry methanol followed by the cautious slow addition of 40 mL of a 1.0 M solution of ethereal hydrogen chloride. After allowing the reaction to proceed for 1 hr, the reaction was poured into mixture of ethyl acetate and water and then the pH was adjusted to 9.5, the layers were separated and the organic layer was dried over $Na_2SO_4$, filtered and concentrated. The resulting product was then recrystallised from $CH_2Cl_2$ and hexane to give 720 mg (91%) of the pure 6-N-methyl quinoline.

Method H:

Exemplary compound 27, 2-(3-fluorophenyl)-N4,N4-dimethyl-quinoline-4,6-diamine, see Table 1 hereafter, was made by the following method. Other compounds prepared by Method H from suitable precursors are listed in Table 1.

H1. 2-(3-Fluorophenyl)-6-nitro-quinolin-4-ol:

Preparation of the title compound is described in Method B.

H2. N-[2-(3-Fluorophenyl)-6-nitro-4-quinolinyl]-N,N-dimethylamine:

The title compound was prepared in a manner analogous to the preparation of N-[6-bromo-2-(3-fluorophenyl)-4-quinolinyl]-N,N-dimethylamine as described in step C5 of Method C.

H3(a). N-[2-(3-Fluorophenyl)-6-amino-4-quinolinyl]-N,N-dimethylamine:

The title compound was prepared by reduction of a nitro group by catalytic hydrogenation as follows. Into a 500 mL Parr shaker bottle was placed 4.0 g of the N-[2-(3-fluorophenyl)-6-nitro-4-quinolinyl]-N,N-dimethylamine along with 150 mg of a catalyst consisting of 5% palladium on calcium carbonate support. To this was added 150 mL of ethanol, followed by application of a 50 psi hydrogen atmosphere. The reaction was shaken for 18 hr then the hydrogen atmosphere was replaced by nitrogen. The catalyst was removed by filtration, and the solution concentrated. The residue was taken up in ethyl acetate, washed with 5% sodium hydroxide solution, then the organic layer was dried over $Na_2SO_4$, filtered and concentrated. The extract was recrystallised from methylene chloride and hexane to give 2.8 g (77%) of the product.

H3(b). Alternative procedure:

Alternatively, N-[2-(3-fluorophenyl)-6-amino-4-quinolinyl]-N,N-dimethylamine was prepared in a manner analogous to the preparation of 2-(3-fluorophenyl)-4,6-quinolinediamine by reduction of the 6-nitro group using stannous chloride as described in step B6 of Method B.

Method I:

Exemplary compound 37, 2-(3-fluorophenyl)-N4,N6-dimethyl-quinoline-4,6-diamine, see Table 1 hereafter, was made by the following method. Other compounds prepared by Method I from suitable precursors are listed in Table 1.

I1. 6-Bromo-4-chloro-2-(3-fluorophenyl)-quinoline:

The title compound was prepared as described in step C4 of Method C.

I2. 2-(3-Fluorophenyl)-N4,N6-dimethyl-4,6-quinolinediamine:

The title compound was prepared by simultaneous Pd catalyzed substitution of 4-chloro and 6-bromo.

Into each of two 4 dram vials equipped with a magnetic stir bar and a teflon-lined septum closure, was placed 1.1 g (3.27 mmoles, 1 equiv.) of 6-bromo-4-chloro-2-(3-fluorophenyl)-quinoline, 73 mg of tris(dibenzylideneacetone) dipalladium(0) (0.08 mmoles, 0.025 equiv., 0.05 equiv. Pd), 397 mg of racemic 2,2'-bis(diphenylphosphino)-1,1'-binapthyl (0.64 mmoles, 0.2 equiv.), 943 mg of sodium tert-butoxide (9.81 mmoles, 3 equiv) and, finally, 10 mL of a 2.0 M solution of methylamine in THF (20 mmoles, 6 equiv). The vials were placed under a nitrogen atmosphere, sealed and then heated to 70° C. in an oil bath for 18 hr. At the end of this time the vials were cooled, combined, and poured into a 1 L separatory funnel containing 300 mL of ethyl acetate and 500 mL of 1 N NaOH solution. The layers were separated and the organic layer was washed again with 500 mL of 1 N NaOH solution. The organic layers were then dried over Na$_2$SO$_4$, filtered and concentrated. The residue was purified by flash chromatography using 5% ethyl acetate in methylene chloride containing 0.5% triethylamine. The fractions containing the desired compound were combined and concentrated and the resulting residue crystallised from methlyene chloride and hexane to give 1.2 g (61%) of product.

Method J:

Exemplary compound 61, 2-(3-dimethylaminophenyl)-N4,N4-dimethyl-quinoline-4,6-diamine, see Table 1 hereafter, was made by the following method. Other compounds prepared by Method J from suitable precursors are listed in Table 1.

J1. N-[2-(3-Chlorophenyl)-6-nitro-4-quinolinyl]-N,N-dimethylamine:

The title compound was prepared in a manner analogous to the preparation of N-[2-(3-fluorophenyl)-6-nitro-4-quinolinyl]-N,N-dimethylamine as described in step H2 of Method H.

J2. 2-(3-Dimethylaminophenyl)-N4,N4-dimethyl-quinoline-4,6-diamine:

The title compound was prepared from N-[2-(3-chlorophenyl)-6-nitro-4-quinolinyl]-N,N-dimethylamine by the procedure of step D2 of Method D using dimethylamine.

Method K:

Exemplary compound 81, 2-(3-chlorophenyl)-N-6-tert-butylcarbamoyl-quinoline-4,6-diamine, M376003, see Table 1 hereafter, was made by the following method. Other compounds prepared by Method K from suitable precursors are listed in Table 1.

K1. [4-Amino-2-(3-chlorophenyl)-quinolin-6-yl]-carbamic Acid Tert-Butyl Ester (6-N-BOC protected):

Into a 250 mL three-neck round-bottom flask equipped with a magnetic stirrer, condenser, addition funnel, heating bath and nitrogen inlet, was added 1.5 g (5.58 mmoles, 1 equiv.) of 2-(3-chlorophenyl)-4,6-quinolinediamine, 50 ml of dry THF, and 3.9 mL (27.9 mmoles, 5 equiv.) of dry triethylamine. To this stirring mixture was then added over 30 min., 6.7 mL (6.69 mmoles, 1.2 equiv.) of di-t-butyl dicarbonate as a solution in 50 mL of THF. The mixture was then heated to reflux for 18 hr., and, at the end of this time, cooled, cautiously quenched with water and partitioned between 300 mL of ethyl acetate and 500 mL of 5% NaOH solution. The organic layer was washed with NaOH solution, dried over Na$_2$SO$_4$, filtered and concentrated. The residue was subjected to flash chromatography, using an eluent of 25% ethyl acetate in methylene chloride containing 0.5% triethylamine to give 1.1 g (53%) of the product.

Method L:

Exemplary compound 25, 2-(3-chlorophenyl)-quinoline-4,6-diamine, see Table 1 hereafter, was made by the following method. Other compounds prepared by Method L from suitable precursors are listed in Table 1.

L1. 2-(3-Chlorophenyl)-4,6-quinolinediamine:

The BOC protecting group was removed by the following procedure. Into a 200 mL round bottom flask equipped with a magnetic stir bar and nitrogen inlet was placed 1.0 g (2.71 mmoles, 1 equiv) of [4-amino-2-(3-chlorophenyl)-quinolin-6-yl]-carbamic acid tert-butyl ester and 60 mL of a 1:2 mixture of trifluoroacetic acid and methylene chloride. The mixture was stirred at room temperature for 3 hrs., then concentrated. The residue was made basic with dilute NaOH solution then extracted with ethyl acetate. The organic layer was washed with NaOH solution, dried over Na$_2$SO$_4$, filtered and concentrated. The residue was crystallised from methylene chloride and hexanes to give 700 mg (95%) of the title compound.

Exemplary Compounds:

Exemplary compounds 1 to 111 inclusive are disclosed in Table 2 which shows the name of each compound and the method of preparation. Where the method of preparation is described as C* compounds were prepared by a method analogous to that of method C, using methylamine in place of dimethylamine.

TABLE 2

| Ex. No. | Name | Method of Preparation |
|---|---|---|
| 1 | 2-(4-Chlorophenyl)-quinoline-4,6-diamine | A |
| 2 | 2,N6-Dimethyl-quinoline-4,6-diamine | G |
| 3 | 2-Phenyl-quinoline-4,6-diamine | A |
| 4 | 2-Phenyl-N4-benzyl-quinoline-4,6-diamine | H |
| 5 | 2-(3-Trifluoromethylphenyl)-quinoline-4,6-diamine | A |
| 6 | 2-Phenyl-N4,N4-dimethyl-quinoline-4,6-diamine | H |
| 7 | 2-Phenyl-N4-propyl-quinoline-4,6-diamine | H |
| 8 | 2-(4-Fluorophenyl)-quinoline-4,6-diamine | A |
| 9 | 2-(3-Methoxyphenyl)-quinoline-4,6-diamine | A |
| 10 | 2-(3-Fluorophenyl)-quinoline-4,6-diamine | A & B |
| 11 | 2-(4-Methoxyphenyl)-quinoline-4,6-diamine | A |
| 12 | 2-Pentyl-quinoline-4,6-diamine | A |
| 13 | 2-(2-Methoxyphenyl)-quinoline-4,6-diamine | A |
| 14 | 2-Phenoxymethyl-quinoline-4,6-diamine | A |
| 15 | 2-(2-Chlorophenyl)-quinoline-4,6-diamine | A |
| 16 | 2-(2-Fluorophenyl)-quinoline-4,6-diamine | A |
| 17 | 2-Phenyl-N6-methyl-quinoline-4,6-diamine | G |
| 18 | 2-(3-Methoxyphenyl)-N6-methyl-quinoline-4,6-diamine | G |
| 19 | 2-(4-Cyclohexylphenyl)-quinoline-4,6-diamine | A |
| 20 | 2-(4-Bromophenyl)-quinoline-4,6-diamine | A |
| 21 | 2-(3-Bromophenyl)-quinoline-4,6-diamine | A |
| 22 | 2-(4-Chlorophenyl)-N6-methyl-quinoline-4,6-diamine | G |
| 23 | 2-(2-Fluorophenyl)-N6-methyl-quinoline-4,6-diamine | G |
| 24 | 2-(3-Fluorophenyl)-N6-methyl-quinoline-4,6-diamine | G |
| 25 | 2-(3-Chlorophenyl)-quinoline-4,6-diamine | A & L |
| 26 | 2-(3-Fluorophenyl)-N4,N4,N6,N6-tetramethyl-quinoline-4,6-diamine | C |
| 27 | 2-(3-Fluorophenyl)-N4,N4-dimethyl-quinoline-4,6-diamine | H |
| 28 | 2-(3-Fluorophenyl)-N4,N4,N6-trimethyl-quinoline-4,6-diamine | C |
| 29 | 2-(3-Fluorophenyl)-N4,N4-dimethyl-N6-cyclopropyl-quinoline-4,6-diamine | C |
| 30 | 2-(3-fluorophenyl)-N4,N4-dimethyl-N6-adamantan-1-yl-quinoline-4,6-diamine | C |
| 31 | 2-(3-fluorophenyl)-N4,N4-dimethyl-N6-ethyl-quinoline-4,6-diamine | C |
| 32 | 2-(3-Fluorophenyl)-N4-morpholin-4-yl-N6-cyclopropyl-quinoline-4,6-diamine | C |
| 33 | 2-(3-Fluorophenyl)-N4,N4-dimethyl-N6-isopropyl-quinoline-4,6-diamine | C |
| 34 | 2-(3-Fluorophenyl)-N4-pyrrolidin-1-yl-N6-cyclopropyl-quinoline-6-amine | C |
| 35 | 2-(3-Fluorophenyl)-N4,N4-dimethyl-N6-cycloheptyl-quinoline-4,6-diamine | C |
| 36 | 2-(3-fluorophenyl)-N4-piperidin-1-yl-N6-cyclopropyl-quinolin-4,6-diamine | C |
| 37 | 2-(3-Fluorophenyl)-N4,N6-dimethyl-quinoline-4,6-diamine | I & C |
| 38 | 2-(3-Fluorophenyl)-N4,N4-dimethyl-6-pyrrolidin-1-yl-quinolin-4-amine | C |
| 39 | 2-(3-Fluorophenyl)-N4-methyl-quinoline-4,6-diamine | H |
| 40 | 2-(3-Fluorophenyl)-N4,N4-dimethyl-N6-(6-amino-pyridin-2-yl)-quinoline-4,6-diamine | C |
| 41 | 2-(3-Fluorophenyl)-N4-methyl-N6-cyclopropyl-quinoline-4,6-diamine | C* |

TABLE 2-continued

| Ex. No. | Name | Method of Preparation |
|---|---|---|
| 42 | 2-(2-Fluorophenyl)-N4,N4-dimethyl-N6-cyclopropyl-quinoline-4,6-diamine | C |
| 43 | 2-(3-Fluorophenyl)-N4,N4-dimethyl-N6-benzothiazol-2-yl-quinoline-4,6-diamine | C |
| 44 | 2-(3-Fluorophenyl)-N4,N4-dimethyl-N6-4-(1,5-dimethyl-2phenyl-1,2-dihydro-pyrazol-3-one)quinoline-4,6-diamine | C |
| 45 | 2-(3-Fluorophenyl)-N4,N4-dimethyl-N6-(2-phenyl-2,5-dihydro-1H-pyrazol-3-yl)-quinoline-4,6-diamine | C |
| 46 | [2-(3-Fluorophenyl)-N4,N4-dimethyl-N6-piperidin-1-yl-quinoline-4,6-diamine | C |
| 47 | 2-(3-Fluorophenyl)-N4,N4-dimethyl-N6-pyrimidin-4-yl-quinoline-4,6-diamine | C |
| 48 | 2-(3-Fluorophenyl)-N4,N4-dimethyl-N6-cyclobutyl-quinoline-4,6-diamine | C |
| 49 | 2-(3-Fluorophenyl)-N4,N4-dimethyl-N6-cyclopropylmethyl-quinoline-4,6-diamine | C |
| 50 | 2-(3-Fluorophenyl)-N4,N4-dimethyl-N6-cyclopentyl-quinoline-4,6-diamine | C |
| 51 | 2-(3-Fluorophenyl)-N4,N4-dimethyl-N6-allyl-quinoline-4,6-diamine | C |
| 52 | 2-(3-Fluorophenyl)-N4,N4-dimethyl-N6-propyl-quinoline-4,6-diamine | C |
| 53 | 2-(3-Chlorophenyl)-N4,N4-dimethyl-N6-cyclopropyl-quinoline-4,6-diamine | C |
| 54 | 2-(3-Fluorophenyl)-N4-(2-methoxy-ethyl)-N6-cyclopropyl-quinoline-4,6-diamine | C |
| 55 | 2-(3-Morpholin-4-ylphenyl)-N4,N4-dimethyl-N6-cyclopropyl-quinoline-4,6-diamine | D |
| 56 | 2-(3-Morpholin-4-ylphenyl)-N4,N4-dimethyl-quinoline-4,6-diamine | E |
| 57 | [2-(3-Fluorophenyl)-N4,N4-dimethyl-6-nitro-quinoline-4-amine | H |
| 58 | [2-(3-Chlorophenyl)-N4,N4-dimethyl-6-nitro-quinoline-4-amine | H |
| 59 | 2-(3-Chlorophenyl)-N4,N4-dimethyl-quinoline-4,6-diamine | H |
| 60 | 2-(3-Fluorophenyl)-N4-methyl-N6-cyclobutyl-quinoline-4,6-diamine | C* |
| 61 | 2-(3-Dimethylaminophenyl)-N4,N4-dimethyl-quinoline-4,6-diamine | J |
| 62 | 2-(3-Methylaminophenyl)-N4-methyl-quinoline-4,6-diamine | J |
| 63 | 2-(3-Fluorophenyl)-N4,N4-dimethyl-N6-(2-methoxy-ethyl)-quinoline-4,6-diamine | C |
| 64 | 2-(3-Fluorophenyl)-N4-ethyl-N6-cyclopropyl-quinoline-4,6-diamine | C* |
| 65 | 2-(3-Methylaminophenyl)-N4,N4-dimethyl-N6-cyclopropyl-quinoline-4,6-diamine | D |
| 66 | 2-(3-Fluorophenyl)-N4,N6-dicyclopropyl-quinoline-4,6-diamine | I |
| 67 | 2-(3-Fluorophenyl)-N4-cyclopropyl-N6-methyl-quinoline-4,6-diamine | C* |
| 68 | 2-(3-Fluorophenyl)-N4,N4-dimethyl-N6-(tetrahydro-furan-2-ylmethyl)-quinoline-4,6-diamine | C |
| 69 | 2-(3-Fluorophenyl)-N4,N4-dimethyl-N6-(2-phenyl-propyl)-quinoline-4,6-diamine | C |
| 70 | 2-(3-fluorophenyl)-N4,N4,N6-trimethyl-N6-Ethyl-quinoline-4,6-diamine | C |
| 71 | 2-(3-Fluorophenyl)-N4,N4-dimethyl-N6-((S)-1-phenyl-ethyl)-quinoline-4,6-diamine | C |
| 72 | 2-(3-Fluorophenyl)-N4-Ethyl-N6-methyl-quinoline-4,6-diamine | C |
| 73 | 2-(3-Chlorophenyl)-N4,N6-dimethyl-quinoline-4,6-diamine | I |
| 74 | 2-(3-Fluorophenyl)-N4-(2-methoxy-ethyl)-N6-methyl-quinoline-4,6-diamine | C* |
| 75 | 2-(3-Chlorophenyl)-N4,N4,N6-trimethyl-quinoline-4,6-diamine | C |
| 76 | 2-(3-Morpholin-4-yl-phenyl)-N4,N6-Dimethyl-quinoline-4,6-diamine | D |
| 77 | 2-(4-Methoxyphenyl)-N6-acetamido-quinoline-4,6-diamine | A |
| 78 | 2-(4-Bromophenyl)-N6-tert-butylcarbamoyl-quinoline-4,6-diamine | K |
| 79 | 2-(2-Fluorophenyl)-N6-acetamido-quinoline-4,6-diamine | F |
| 80 | 2-(3-Bromophenyl)-N6-tert-butylcarbamoyl-quinoline-4,6-diamine | K |
| 81 | 2-(3-Chlorophenyl)-N6-tert-butylcarbamoyl-quinoline-4,6-diamine | K |
| 82 | 2-(2-Chlorophenyl)-N6-tert-butylcarbamoyl-quinoline-4,6-diamine | K |
| 83 | 2-(3-Fluorophenyl)-N6-tert-butylcarbamoyl-quinoline-4,6-diamine | K |
| 84 | 2-(3-Fluorophenyl)-N4,N4-dimethyl-N6-(4-methoxyphenyl)-quinoline-4,6-diamine | C |
| 85 | 2-(3-Fluorophenyl)-N4,N4-dimethyl-N6-(3-aminophenyl)quinoline-4,6-diamine | C |
| 86 | 2-(3-Fluorophenyl)-N4,N4-dimethyl-quinoline-4-amine-6-acetamide | H & F |
| 87 | 2-[3-(4-Morpholinyl)phenyl]-N4,N4,N6-trimethyl-quinoline-4,6-diamine | C & J |
| 88 | 2-[3-(Methylamino)phenyl]-N4,N6-dimethyl-quinoline-4,6-diamine | C* & J |
| 89 | 2-(3-Chlorophenyl)-N4-methyl-N6-cyclopropyl-quinoline-4,6-diamine | C* |
| 90 | 2-[3-(4-Morpholinyl)phenyl]-N4-methyl-N6-cyclopropyl-quinoline-4,6-diamine | C* & J |
| 91 | 2-(3-Fluorophenyl)-N4,N4-dimethyl-N6-cyclopropyl-N6-acetyl-quinoline-4,6-diamine | C & F |
| 92 | 2-(3-Fluorophenyl)-N4-methyl-N6-cyclopropyl-N6-acetyl-quinoline-4,6-diamine | C* & F |
| 93 | 2-(3-Fluorophenyl)-N4,N4-dimethyl-N6-methyl-N6-acetyl-quinoline-4,6-diamine | I & F |
| 94 | N6-Cyclopentyl-2-(3-fluorophenyl)-N4-methyl-4,6-quinolinediamine | C* |
| 95 | N6,2-bis(3-fluorophenyl)-N4,N4-dimethyl-4,6-quinolinediamine | C |
| 96 | N6-(3-chloro-4-methylphenyl)-2-(3-fluorophenyl)-N4,N4-dimethyl-4,6-quinolinediamine | C |
| 97 | 2-(3-Fluorophenyl)-N4,N4-dimethyl-N6-(2-methyl-1H-isoindole-1,3(2H)-dione-5-yl)-quinoline-4,6-diamine | C |
| 98 | 2-(3-Fluorophenyl)-N4,N4-dimethyl-N6-(2,6-dichlorophenyl)-quinoline-4,6-diamine | C |
| 99 | 2-(3-Fluorophenyl)-N4-methyl-N6-acetyl-quinoline-4,6-diamine | H & F |
| 100 | 2-(3-Fluorophenyl)-N4,N4-dimethyl-N6-(2-chloro-6-methylphenyl)-quinoline-4,6-diamine | C |
| 101 | 2-(3-Fluorophenyl)-N4,N4-dimethyl-N6-(3,5-dimethoxyphenyl)-quinoline-4,6-diamine | C |
| 102 | 2-(3-Fluorophenyl)-N4,N4-dimethyl-N6-(3,4-dichlorophenyl)-quinoline-4,6-diamine | C |
| 103 | 2-(3-Fluorophenyl)-N4,N4-dimethyl-N6-(3-fluoro-4-methylphenyl)-quinoline-4,6-diamine | C |
| 104 | 2-(3-Fluorophenyl)-N4,N4-dimethyl-N6-(4-methylphenyl)-quinoline-4,6-diamine | C |
| 105 | 2-(3-Fluorophenyl)-N4,N4-dimethyl-N6-(4-chlorophenyl)-quinoline-4,6-diamine | C |
| 106 | 2-(3-Fluorophenyl)-N4,N4-dimethyl-N6-(3-ethylphenyl)-quinoline-4,6-diamine | C |
| 107 | 2-(3-Fluorophenyl)-N4,N4-dimethyl-N6-(1-methyl-cyclopropyl)-quinoline-4,6-diamine | C |
| 108 | 2-(3-Fluorophenyl)-N4-methyl-N6-(1-methyl-cyclopropyl)-quinoline-4,6-diamine | C* |
| 109 | 2-(3-Fluorophenyl)-N4,N4-dimethyl-N6-(1-methyl-cyclobutyl)-quinoline-4,6-diamine | C |
| 110 | 2-(3-Fluorophenyl)-N4-methyl-N6-(1-methyl-cyclobutyl)-quinoline-4,6-diamine | C* |
| 111 | 2-(3-Fluorophenyl)-N4-methyl-N6-(iso-propyl)-quinoline-4,6-diamine | C* |

Exemplary compounds 1 to 111 inclusive are illustrated in Table 3 which shows the mass spectroscopy data and the elemental analysis determined for certain compounds.

TABLE 3

| Ex. No. | Formula | M + 1 | Anal. Calc. for | Theor. | Found |
|---|---|---|---|---|---|
| 1 | $C_{15}H_{12}ClN_3$ | 270/272(+) | $C_{15}H_{12}ClN_3$ 0.05 $CH_2Cl_2$ | C, 65.98; H, 4.45; N, 15.34 | C, 66.00; H, 4.69; N, 15.00 |
| 2 | $C_{11}H_{13}N_3$ | 188(+) | $C_{11}H_{13}N_3$ 0.046 $CH_2Cl_2$ | C, 69.41; H, 6.90; N, 21.98 | C, 69.73; H, 6.95; N, 21.60 |
| 3 | $C_{15}H_{13}N_3$ | 236(+) | $C_{15}H_{13}N_3$ 0.03 $CH_2Cl_2$ | C, 75.90; H, 5.36; N, 17.67 | C, 75.46; H, 5.74; N, 17.37 |
| 4 | $C_{22}H_{19}N_3$ | 326(+) | $C_{22}H_{19}N_3$ 0.12 $CH_2Cl_2$ | C, 79.17; H, 5.78; N, 12.52 | C, 78.48; H, 5.86; N, 12.51 |
| 5 | $C_{16}H_{12}F_3N_3$ | 304(+) | $C_{16}H_{12}F_3N_3$ 0.12 $CH_2Cl_2$ | C, 62.42; H, 3.96; N, 13.58 | C, 62.58; H, 4.11; N, 13.28 |
| 6 | $C_{17}H_{17}N_3$ | 264(+) | $C_{17}H_{17}N_3$ 0.25 $H_2O$ | C, 76.23; H, 6.59; N, 15.69 | C, 76.34; H, 6.57; N, 15.35 |
| 7 | $C_{18}H_{19}N_3$ | 278(+) | $C_{18}H_{19}N_3$ 0.20 $H_2O$ | C, 76.95; H, 6.96; N, 14.96 | C, 76.66; H, 6.96; N, 14.96 |
| 8 | $C_{15}H_{12}FN_3$ | 254(+) | $C_{15}H_{12}FN_3$ 0.20 $H_2O$ 0.10 $C_4H_8O_2$ | C, 69.62; H, 5.01; N, 15.81 | C, 69.78; H, 5.03; N, 15.55 |
| 9 | $C_{16}H_{15}N_3O$ | 266(+) | $C_{16}H_{15}N_3O$ 0.10 $H_2O$ | C, 71.95; H, 5.74; N, 15.73 | C, 71.86; H, 5.68; N, 15.89 |
| 10 | $C_{15}H_{12}FN_3$ | 254(+) | $C_{15}H_{12}FN_3$ 0.15 $H_2O$ | C, 70.38; H, 4.84; N, 16.42 | C, 69.65; H, 4.77; N, 16.65 |
| 11 | $C_{16}H_{15}N_3O$ | 266(+) | $C_{16}H_{15}N_3O$ 0.08 $CH_2Cl_2$ | C, 70.98; H, 5.62; N, 15.44 | C, 71.10; H, 5.60; N, 15.62 |
| 12 | $C_{14}H_{19}N_3$ | 230(+) | $C_{14}H_{19}N_3$ | C, 73.32; H, 8.35; N, 18.32 | C, 73.51; H, 8.32; N, 18.07 |
| 13 | $C_{16}H_{15}N_3O$ | 266(+) | $C_{16}H_{15}N_3O$ 0.07 $CH_2Cl_2$ | C, 71.16; H, 5.63; N, 15.49 | C, 71.40; H, 5.84; N, 15.18 |
| 14 | $C_{16}H_{15}N_3O$ | 266(+) | $C_{16}H_{15}N_3O$ 0.10 $CH_2Cl_2$ | C, 70.62; H, 5.60; N, 15.34 | C, 70.58; H, 5.60; N, 15.11 |
| 15 | $C_{15}H_{12}ClN_3$ | 270/272(+) | $C_{15}H_{12}ClN_3$ 0.30 $C_4H_8O_2$ | C, 65.70; H, 4.90; N, 14.19 | C, 65.45; H, 4.93; N, 14.52 |
| 16 | $C_{15}H_{12}FN_3$ | 254(+) | $C_{15}H_{12}FN_3$ | C, 71.13; H, 4.78; N, 16.59 | C, 71.00; H, 4.98; N, 16.39 |
| 17 | $C_{16}H_{15}N_3$ | 250(+) | $C_{16}H_{15}N_3$ 0.10 $CH_2Cl_2$ 0.10 $C_6H_{14}$ | C, 75.29; H, 6.28; N, 15.77 | C, 75.09; H, 6.29; N, 15.42 |
| 18 | $C_{17}H_{17}N_3O$ | 280(+) | $C_{17}H_{17}N_3O$ 0.20 $CH_2Cl_2$ | C, 69.72; H, 5.92; N, 14.18 | C, 69.67; H, 6.17; N, 13.92 |
| 19 | $C_{21}H_{23}N_3$ | 318(+) | $C_{21}H_{23}N_3$ 0.30 $CH_4O$ | C, 78.23; H, 7.46; N, 12.85 | C, 78.08; H, 7.21; N, 12.96 |
| 20 | $C_{15}H_{12}BrN_3$ | 314/316(+) | $C_{15}H_{12}BrN_3$ 0.10 $CH_2Cl_2$ 0.10 $C_6H_{14}$ | C, 56.92; H, 4.14; N, 12.68 | C, 56.93; H, 4.11; N, 12.47 |
| 21 | $C_{15}H_{12}BrN_3$ | 314/316(+) | $C_{15}H_{12}BrN_3$ 0.15 $CH_2Cl_2$ | C, 55.66; H, 3.79; N, 12.85 | C, 55.49; H, 4.07; N, 13.02 |
| 22 | $C_{16}H_{14}ClN_3$ | 284/286(+) | $C_{16}H_{14}ClN_3$ 0.20 $CH_2Cl_2$ 0.15 $C_6H_{14}$ | C, 65.49; H, 5.30; N, 13.40 | C, 65.34; H, 5.28; N, 13.53 |
| 23 | $C_{16}H_{14}FN_3$ | 268(+) | $C_{16}H_{14}FN_3$ 0.27 $H_2O$ | C, 70.61; H, 5.39; N, 15.43 | C, 70.91; H, 5.57; N, 15.04 |
| 24 | $C_{16}H_{14}FN_3$ | 268(+) | $C_{16}H_{14}FN_3$ 0.22 $CH_2Cl_2$ 0.20 $C_6H_{14}$ | C, 69.00; H, 5.73; N, 13.85 | C, 69.04; H, 5.45; N, 13.89 |
| 25 | $C_{15}H_{12}ClN_3$ | 270/272(+) | $C_{15}H_{12}ClN_3$ | C, 66.79; H, 4.48; N, 15.58 | C, 66.78; H, 4.51; N, 15.27 |
| 26 | $C_{19}H_{20}FN_3$ | 310(+) | $C_{19}H_{20}FN_3$ 2.00 HCl | C, 59.69; H, 5.80; N, 10.99 | C, 59.51; H, 6.04; N, 10.65 |
| 27 | $C_{17}H_{16}FN_3$ | 282(+) | $C_{17}H_{16}FN_3$ | C, 72.57; H, 5.73; N, 14.94 | C, 72.64; H, 5.74; N, 14.82 |
| 28 | $C_{18}H_{18}FN_3$ | 296(+) | $C_{18}H_{18}FN_3$ 2.00 HCl | C, 57.30; H, 5.61; N, 11.13 | C, 57.44; H, 5.51; N, 11.04 |
| 29 | $C_{20}H_{20}FN_3$ | 322(+) | $C_{20}H_{20}FN_3$ | C, 74.74; H, 6.27; N, 13.07 | C, 74.41; H, 6.26; N, 12.73 |
| 30 | $C_{27}H_{30}FN_3$ | 416(+) | $C_{27}H_{30}FN_3$ 0.02 $CH_2Cl_2$ 0.15 $C_6H_{14}$ | C, 77.96; H, 7.53; N, 9.77 | C, 78.20; H, 7.16; N, 9.40 |
| 31 | $C_{19}H_{20}FN_3$ | 310(+) | $C_{19}H_{20}FN_3$ 0.04 $CH_2Cl_2$ | C, 73.43; H, 6.49; N, 13.57 | C, 73.18; H, 6.49; N, 13.18 |
| 32 | $C_{22}H_{22}FN_3O$ | 364(+) | $C_{22}H_{22}FN_3O$ | C, 72.71; H, 6.10; N, 11.56 | C, 72.50; H, 6.10; N, 11.83 |
| 33 | $C_{20}H_{22}FN_3O$ | 324(+) | $C_{20}H_{22}FN_3O$ 3.00 HCl | C, 55.50; H, 5.82; N, 9.70 | C, 55.79; H, 5.69; N, 9.41 |
| 34 | $C_{22}H_{22}FN_3$ | 348(+) | $C_{22}H_{22}FN_3$ 0.10 $CH_2Cl_2$ 0.05 $C_6H_{14}$ | C, 74.69; H, 6.41; N, 11.67 | C, 74.71; H, 6.28; N, 11.31 |
| 35 | $C_{24}H_{28}FN_3$ | 378(+) | | | |
| 36 | $C_{23}H_{24}FN_3$ | 362(+) | $C_{23}H_{24}FN_3$ 0.10 $CH_2Cl_2$ | C, 74.99; H, 6.59; N, 11.34 | C, 74.95; H, 6.67; N, 11.17 |
| 37 | $C_{17}H_{16}FN_3$ | 282(+) | $C_{17}H_{16}FN_3$ | C, 72.58; H, 5.73; N, 14.94 | C, 72.67; H, 5.73; N, 14.85 |
| 38 | $C_{21}H_{22}FN_3$ | 336(+) | $C_{21}H_{22}FN_3$ | C, 70.50; H, 4.89; N, 10.72 | C, 70.25; H, 5.10; N, 10.54 |
| 39 | $C_{16}H_{14}FN_3$ | 268(+) | $C_{16}H_{14}FN_3$ 0.16 $H_2O$ 0.02 $C_6H_{14}$ | C, 71.21; H, 5.41; N, 15.45 | C, 71.49; H, 5.45; N, 15.09 |
| 40 | $C_{22}H_{20}FN_5$ | 374(+) | $C_{22}H_{20}FN_5$ 0.20 $H_2O$ | C, 70.08; H, 5.45; N, 18.56 | C, 70.23; H, 5.47; N, 18.51 |
| 41 | $C_{19}H_{18}FN_3$ | 308(+) | $C_{19}H_{18}FN_3$ 0.10 $CH_2Cl_2$ | C, 72.62; H, 5.81; N, 13.30 | C, 72.91; H, 5.85; N, 13.40 |
| 42 | $C_{20}H_{20}FN_3$ | 322(+) | $C_{20}H_{20}FN_3$ 0.16 $H_2O$ 0.10 $C_6H_{14}$ | C, 74.71; H, 6.71; N, 12.47 | C, 74.91; H, 6.32; N, 12.09 |
| 43 | $C_{24}H_{19}FN_4S$ | | | | |
| 44 | $C_{28}H_{26}FN_5O$ | 466(−) | | | |
| 45 | $C_{26}H_{22}FN_5$ | 424(+) | | | |
| 46 | $C_{22}H_{24}FN_3$ | 350(+) | $C_{22}H_{24}FN_3$ 2.00 HCl 0.40 $H_2O$ | C, 61.51; H, 6.29; N, 9.78 | C, 61.61; H, 6.22; N, 9.77 |
| 47 | $C_{21}H_{18}FN_5$ | 360(+) | $C_{21}H_{18}FN_5$ 0.05 $CH_2Cl_2$ 0.15 $C_6H_{14}$ | C, 70.01; H, 5.41; N, 18.60 | C, 70.22; H, 5.05; N, 18.62 |
| 48 | $C_{21}H_{22}FN_3$ | 336(+) | $C_{21}H_{22}FN_3$ 0.10 $C_6H_{14}$ | C, 76.30; H, 5.75; N, 12.35 | C, 76.77; H, 5.76; N, 11.97 |
| 49 | $C_{21}H_{22}FN_3$ | 336(+) | $C_{21}H_{22}FN_3$ 0.05 $C_6H_{14}$ | C, 75.30; H, 6.73; N, 12.37 | C, 75.31; H, 6.68; N, 11.99 |
| 50 | $C_{22}H_{24}FN_3$ | 350(+) | $C_{22}H_{24}FN_3$ 0.10 $C_6H_{14}$ | C, 75.81; H, 7.15; N, 11.73 | C, 76.12; H, 6.96; N, 11.53 |
| 51 | $C_{20}H_{20}FN_3$ | 322(+) | $C_{20}H_{20}FN_3$ | C, 74.74; H, 6.27; N, 13.07 | C, 74.94; H, 6.30; N, 12.71 |
| 52 | $C_{20}H_{22}FN_3$ | 324(+) | $C_{20}H_{22}FN_3$ 0.05 $CH_2Cl_2$ 0.05 $C_6H_{14}$ | C, 73.63; H, 6.92; N, 12.65 | C, 73.76; H, 6.77; N, 12.28 |
| 53 | $C_{20}H_{20}ClN_3$ | 338/340(+) | $C_{20}H_{20}ClN_3$ 0.015 $CH_2Cl_2$ | C, 70.86; H, 5.95; N, 12.39 | C, 71.06; H, 5.99; N, 12.22 |

TABLE 3-continued

| Ex. No. | Formula | M + 1 | Anal. Calc. for | Theor. | Found |
|---|---|---|---|---|---|
| 54 | $C_{21}H_{22}FN_3O$ | 352(+) | $C_{21}H_{22}FN_3O$ 0.03 $CH_2Cl_2$ | C, 71.36; H, 6.28; N, 11.87 | C, 71.31; H, 6.26; N, 12.15 |
| 55 | $C_{24}H_{28}N_4O$ | 389(+) | $C_{24}H_{28}N_4O$ 0.03 $CH_2Cl_2$ 0.25 $C_6H_{14}$ | C, 74.32; H, 7.71; N, 13.58 | C, 74.59; H, 7.34; N, 13.23 |
| 56 | $C_{21}H_{28}N_4O$ | 349(+) | $C_{21}H_{28}N_4O$ 0.25 $CH_2Cl_2$ 0.08 $C_6H_{14}$ | C, 71.98; H, 7.40; N, 14.87 | C, 72.07; H, 7.12; N, 14.70 |
| 57 | $C_{17}H_{14}FN_3O_2$ | 312(+) | $C_{17}H_{14}FN_3O_2$ 0.10 $H_2O$ | C, 65.21; H, 4.57; N, 13.42 | C, 65.10; H, 4.48; N, 13.25 |
| 58 | $C_{17}H_{14}ClN_3O$ | 328/330(+) | $C_{17}H_{14}ClN_3O_2$ | C, 62.29; H, 4.31; N, 12.82 | C, 62.33; H, 4.24; N, 12.70 |
| 59 | $C_{17}H_{16}ClN_3$ | 298/300(+) | $C_{17}H_{16}ClN_3$ | C, 68.56; H, 5.42; N, 14.11 | C, 68.33; H, 5.40; N, 13.91 |
| 60 | $C_{20}H_{20}FN_3$ | 322(+) | $C_{20}H_{20}FN_3$ 0.10 $C_6H_{14}$ | C, 74.97; H, 6.53; N, 12.73 | C, 75.29; H, 6.30; N, 12.91 |
| 61 | $C_{19}H_{22}N_4$ | 307(+) | $C_{19}H_{22}N_4$ 0.12 $CH_2Cl_2$ 0.06 $C_6H_{14}$ | C, 73.82; H, 7.45; N, 17.41 | C, 73.78; H, 7.28; N, 17.07 |
| 62 | $C_{17}H_{18}N_4$ | 279(+) | $C_{17}H_{18}N_4$ 0.03 $CH_2Cl_2$ 0.25 $C_6H_{14}$ 0.30 $CH_4O$ | C, 71.63; H, 6.57; N, 19.15 | C, 71.75; H, 6.52; N, 18.94 |
| 63 | $C_{20}H_{22}FN_3O$ | 340(+) | $C_{20}H_{22}FN_3O$ | C, 70.78; H, 6.53; N, 12.38 | C, 70.71; H, 6.56; N, 12.09 |
| 64 | $C_{20}H_{20}FN_3$ | 322(+) | $C_{20}H_{20}FN_3$ 0.05 $CH_2Cl_2$ | C, 73.95; H, 6.22; N, 12.90 | C, 73.89; H, 6.22; N, 12.58 |
| 65 | $C_{17}H_{18}N_4$ | 333(+) | $C_{17}H_{18}N_4$ 0.32 $CH_2Cl_2$ 0.04 $C_6H_{14}$ | C, 75.88; H, 7.92; N, 15.42 | C, 76.03; H, 7.53; N, 15.19 |
| 66 | $C_{21}H_{20}FN_3$ | 334(+) | $C_{21}H_{20}FN_3$ 0.12 $CH_2Cl_2$ | C, 73.83; H, 5.94; N, 12.23 | C, 73.74; H, 5.94; N, 12.01 |
| 67 | $C_{19}H_{18}FN_3$ | 308(+) | $C_{19}H_{18}FN_3$ | C, 74.25; H, 5.90; N, 13.67 | C, 74.19; H, 6.01; N, 13.33 |
| 68 | $C_{22}H_{24}FN_3O$ | 366(+) | $C_{22}H_{24}FN_3O$ 1.00 HCl | | |
| 69 | $C_{26}H_{26}FN_3$ | 400(+) | $C_{26}H_{26}FN_3$ 1.00 HCl | | |
| 70 | $C_{20}H_{22}FN_3$ | 324(+) | $C_{20}H_{22}FN_3$ 1.00 HCl | | |
| 71 | $C_{25}H_{24}FN_3$ | 386(+) | $C_{25}H_{24}FN_3$ 1.00 HCl | | |
| 72 | $C_{18}H_{18}FN_3$ | 296(+) | $C_{18}H_{18}FN_3$ 0.14 $CH_2Cl_2$ 0.05 $C_6H_{14}$ | C, 72.17; H, 6.44; N, 13.34 | C, 72.30; H, 6.07; N, 12.95 |
| 73 | $C_{17}H_{16}ClN_3$ | 298/300(+) | $C_{17}H_{16}ClN_3$ 0.10 $CH_2Cl_2$ 0.08 $C_6H_{14}$ | C, 67.80; H, 5.65; N, 13.42 | C, 67.76; H, 5.39; N, 13.28 |
| 74 | $C_{19}H_{20}FN_3O$ | 326(+) | $C_{19}H_{20}FN_3O$ 0.08 $CH_2Cl_2$ | C, 68.99; H, 6.12; N, 12.65 | C, 68.96; H, 6.08; N, 12.45 |
| 75 | $C_{18}H_{18}ClN_3$ | 312/314(+) | $C_{18}H_{18}ClN_3$ 0.13 $C_6H_{14}$ | C, 69.83; H, 6.19; N, 13.01 | C, 70.16; H, 5.88; N, 12.88 |
| 76 | $C_{21}H_{24}N_4O$ | 349(+) | $C_{21}H_{24}N_4O$ | C, 68.76; H, 6.85; N, 14.65 | C, 68.30; H, 6.92; N, 14.42 |
| 77 | $C_{18}H_{17}N_3O_2$ | 308(+) | $C_{18}H_{17}N_3O_2$ 0.22 $C_4H_8O$ 0.15 $CH_2Cl_2$ | C, 66.28; H, 5.59; N, 12.14 | C, 66.56; H, 5.72; N, 11.75 |
| 78 | $C_{20}H_{20}BrN_3O_2$ | 414/416(+) | $C_{20}H_{20}BrN_3O_2$ | C, 57.98; H, 4.87; N, 10.14 | C, 57.79; H, 4.90; N, 9.99 |
| 79 | $C_{17}H_{14}FN_3O$ | 296(+) | $C_{17}H_{14}FN_3O$ | C, 69.14; H, 4.78; N, 14.23 | C, 69.05; H, 4.90; N, 13.89 |
| 80 | $C_{20}H_{20}BrN_3O_2$ | 414/416(+) | $C_{20}H_{20}BrN_3O_2$ | C, 57.98; H, 4.87; N, 10.14 | C, 58.16; H, 4.95; N, 10.16 |
| 81 | $C_{20}H_{20}ClN_3O_2$ | 370/372(+) | $C_{20}H_{20}ClN_3O_2$ | C, 64.95; H, 5.45; N, 11.36 | C, 65.03; H, 5.54; N, 11.37 |
| 82 | $C_{20}H_{20}ClN_3O_2$ | 370/372(+) | $C_{20}H_{20}ClN_3O_2$ 0.20 $CH_2Cl_2$ | C, 62.72; H, 5.32; N, 10.86 | C, 62.57; H, 5.39; N, 10.73 |
| 83 | $C_{20}H_{20}FN_3O_2$ | 354(+) | $C_{20}H_{20}FN_3O_2$ | C, 67.98; H, 5.70; N, 11.89 | C, 67.87; H, 5.73; N, 11.67 |
| 84 | $C_{24}H_{22}FN_3O$ | 388(+) | $C_{24}H_{22}FN_3O$ 0.05 $CH_2Cl_2$ | C, 73.75; H, 5.69; N, 10.72 | C, 73.54; H, 5.80; N, 10.62 |
| 85 | $C_{23}H_{21}FN_4$ | 373(+) | $C_{23}H_{21}FN_4$ 0.10 $H_2O$ | C, 73.82; H, 5.71; N, 14.97 | C, 73.58; H, 5.75; N, 14.91 |
| 86 | $C_{19}H_{18}FN_3O$ | 324(+) | $C_{19}H_{18}FN_3O$ 0.50 $CH_2Cl_2$ | C, 64.02; H, 5.23; N, 11.49 | C, 63.62; H, 5.26; N, 11.49 |
| 87 | $C_{22}H_{26}N_4O$ | 363(+) | $C_{22}H_{26}N_4O$ 0.30 $C_6H_{14}$ | C, 73.61; H, 7.84; N, 14.43 | C, 73.86; H, 7.53; N, 14.57 |
| 88 | $C_{18}H_{20}N_4$ | 293(+) | $C_{18}H_{20}N_4$ 0.03 $C_4H_8O_2$ 0.03 $C_6H_{14}$ | C, 73.86; H, 6.99; N, 18.83 | C, 73.99; H, 6.98; N, 18.50 |
| 89 | $C_{19}H_{18}ClN_3$ | 324(+) | $C_{19}H_{18}ClN_3$ 0.02 $CH_2Cl_2$ 0.08 $C_6H_{14}$ | C, 70.53; H, 5.86; N, 12.58 | C, 70.67; H, 5.54; N, 12.23 |
| 90 | $C_{23}H_{26}N_4O$ | 375(+) | $C_{23}H_{26}N_4O$ 0.12 $C_6H_{14}$ | C, 74.03; H, 7.25; N, 14.56 | C, 73.88; H, 7.19; N, 14.24 |
| 91 | $C_{22}H_{22}FN_3O$ | 364(+) | $C_{22}H_{22}FN_3O$ 0.10 $C_6H_{14}$ | | |
| 92 | $C_{21}H_{20}FN_3O$ | 350(+) | $C_{21}H_{20}FN_3O$ 0.15 $H_2O$ 0.02 $C_6H_{14}$ | C, 71.69; H, 5.86; N, 11.87 | C, 71.78; H, 5.67; N, 11.49 |
| 93 | $C_{19}H_{18}FN_3O$ | 324(+) | $C_{19}H_{18}FN_3O$ | C, 70.57; H, 5.61; N, 12.99 | C, 70.71; H, 5.74; N, 13.02 |
| 94 | $C_{21}H_{22}FN_3$ | 336(+) | $C_{21}H_{22}FN_3$ 0.10 $C_6H_{14}$ | C, 75.47; H, 6.85; N, 12.28 | C, 75.68; H, 6.51; N, 12.28 |
| 95 | $C_{23}H_{19}F_2N_3$ | 376(+) | $C_{23}H_{19}F_2N_3$ 0.20 $H_2O$ | C, 72.89; H, 5.16; N, 11.09 | C, 72.98; H, 5.13; N, 10.92 |
| 96 | $C_{24}H_{21}ClFN_3$ | 406/408(+) | $C_{24}H_{21}ClFN_3$ | C, 71.02; H, 5.22; N, 10.35 | C, 70.85; H, 5.25; N, 10.17 |
| 97 | $C_{26}H_{21}FN_4O_2$ | 441(+) | $C_{26}H_{21}FN_4O_2$ 1.00 HCl | | |
| 98 | $C_{23}H_{18}Cl_2FN_3$ | 426/428(+) | $C_{23}H_{18}Cl_2FN_3$ 2.00 HCl | | |
| 99 | $C_{18}H_{16}FN_3O$ | 310(+) | $C_{18}H_{16}FN_3O$ 0.15 $C_4H_8O_2$ | C, 69.26; H, 5.38; N, 13.03 | C, 69.12; H, 5.38; N, 12.98 |
| 100 | $C_{24}H_{21}ClFN_3$ | 406/408(+) | $C_{24}H_{21}ClFN_3$ 1.00 HCl | | |
| 101 | $C_{25}H_{24}FN_3O_2$ | 418(+) | | | |
| 102 | $C_{23}H_{18}Cl_2FN_3$ | 426/428(+) | | | |
| 103 | $C_{24}H_{21}F_2N_3$ | 390(+) | | | |
| 104 | $C_{24}H_{22}FN_3$ | 372(+) | | | |
| 105 | $C_{23}H_{19}ClFN_3$ | 392/394(+) | | | |
| 106 | $C_{25}H_{24}FN_3$ | 386(+) | $C_{25}H_{24}FN_3$ 0.04 $C_6H_{14}$ | C, 75.28; H, 6.71; N, 12.40 | C, 75.59; H, 6.31; N, 12.23 |
| 107 | $C_{21}H_{22}FN_3$ | 336(+) | | | |
| 108 | $C_{20}H_{20}FN_3$ | 322(+) | | | |
| 109 | $C_{22}H_{24}FN_3$ | 350(+) | | | |
| 110 | $C_{24}H_{22}FN_3$ | 336(+) | | | |
| 111 | $C_{19}H_{20}FN_3$ | 310(+) | $C_{25}H_{24}FN_3$ 0.15 $C_6H_{14}$ | C, 74.16; H, 6.91; N, 13.04 | C, 74.54; H, 6.53; N, 13.23 |

The invention claimed is:

1. A compound in accord with structural diagram I

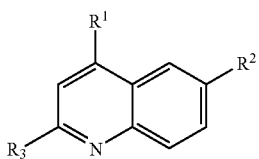

wherein:
R$^1$ is selected from E$^1$ and E$^2$ wherein:
E$^1$ is N(R$^4$)$_2$ where R$^4$ at each occurrence is selected from hydrogen, benzyl, C$_{1-6}$alkyl, C$_{3-7}$cycloakyl, methoxyC$_{1-4}$alkyl; and
E$^2$ is morpholinyl;
R$^2$ is NHR$^5$ where R$^5$ is selected from pyrimidin-4-yl, 1-phenylethyl, and 2-phenylpropyl; and
R$^3$ is selected from C$_{1-6}$alkyl, phenoxyC$_{1-3}$alkyl or phenyl substituted wit E$^5$, where E$^5$ is selected from hydrogen, halogen, C$_{1-6}$alkoxy, C$_{3-7}$cycloalkyl, morpholinyl, C$_{1-4}$perfluoroalkyl, NHC$_{1-3}$alkyl and N(C$_{1-3}$alkyl)$_2$.

2. A compound according to claim 1 having a structure in accord with structural diagram II, III or IV

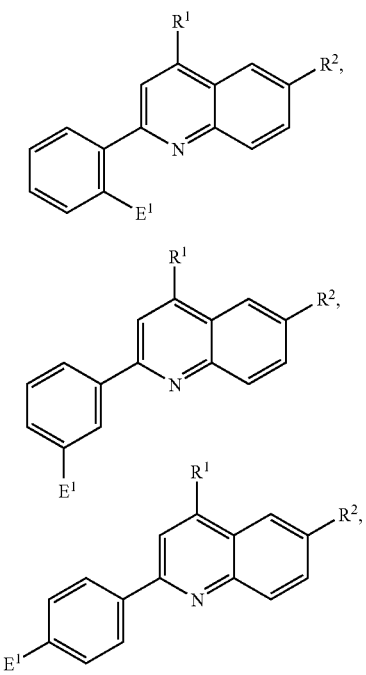

wherein R$^1$, R$^2$ and E$^5$ are as defined in claim 1.

3. A compound according to claim 2 having a structure in accord with structural diagram III wherein:
E$^5$ is halogen and R$^1$ and R$^2$ are as defined in claim 2.

4. A compound according to claim 3 wherein:
E$^5$ is fluoro.

5. A method for the treatment of pain in a subject suffering therefrom, comprising administering to said subject a pain-ameliorating effective amount of a compound according to claim 1.

6. A pharmaceutical composition comprising a therapeutically-effective amount of a compound according to claim 1 together with a pharmaceutically-acceptable excipient or diluent.

7. A method for preparing a compound according to claim 1, said method comprising:
a) preparing 3-substituted-3-oxo-propionic acid ethyl ester (β-keto ester) according to structural diagram V as follows:

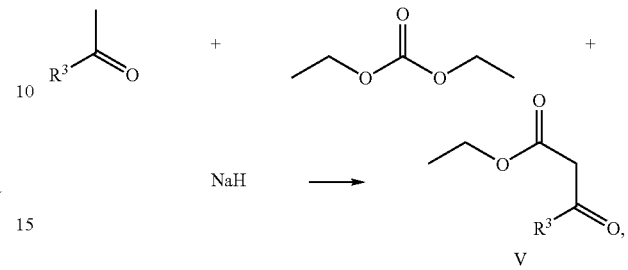

wherein R$^3$ is as defined in claim 1;
b) converting said β-keto ester of structural diagram V to an enamine according to structural diagram VI as follows

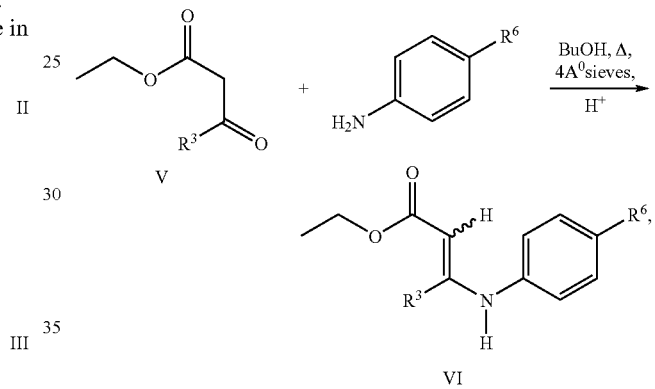

wherein R$^6$ is a group selected from —NH—CO—CH$_3$, NO$_2$ and Br;
c) cyclizing said enamine of structural diagram VI to form a compound according to structural diagram VII as follows

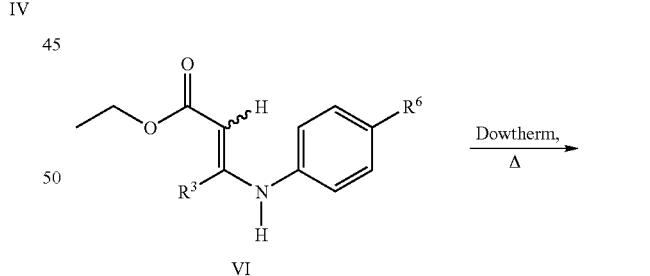

d) when R$^6$ —NH—CO—CH$_3$, convening a compound of structural diagram VII to a compound according to structural diagram I by the process of the following scheme:

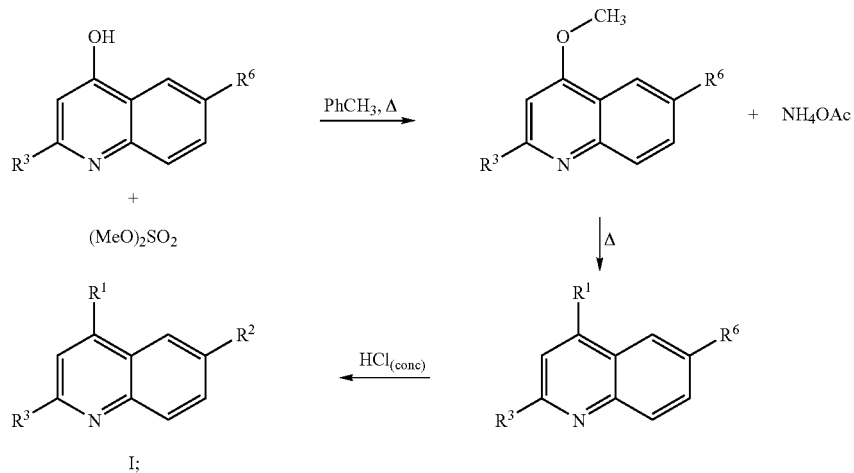
or,
when R⁶ is —NO₂, converting a compound of structural diagram VII to a compound according to structural diagram I, wherein $R^1$ and $R^2$ are both $NH_2$, by the process of the following scheme:
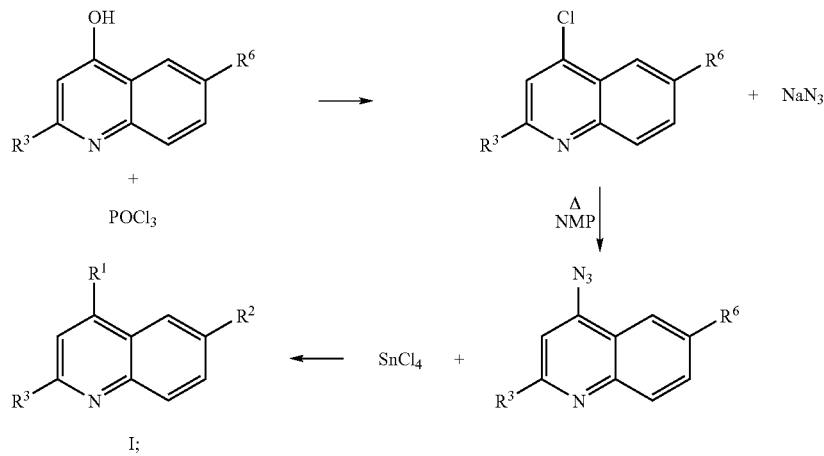
or,
when R⁶ is —Br, converting a compound of structural diagram VII to a compound according to structural diagram I, wherein $R^2$ is $E^{3}$, by the process of the following scheme:
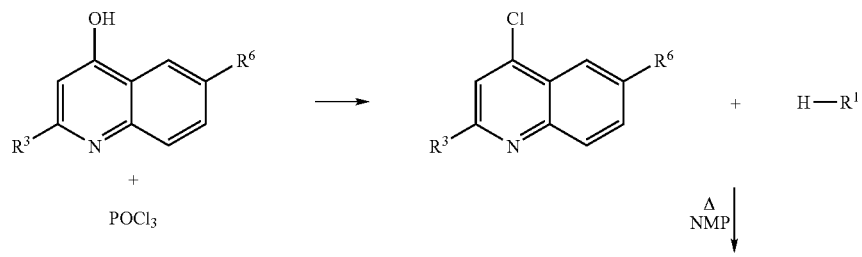

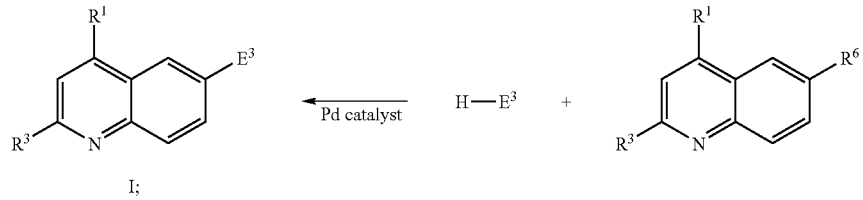

wherein, if necessary, in steps a), b), c) and d) any functional group is protected with a protecting group, and thereafter, e) removing any said protecting group;

f) convening one compound according to structural diagram I to another compound according to structural diagram I by procedures described in Methods A through L herein, and g) purifying said compound of structural diagram I to the extent necessary and, if necessary, forming a pharmaceutically-acceptable salt.

8. A compound in accord with structural diagram I

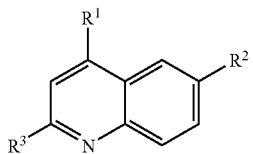

wherein:

R¹ is selected from E¹ and E² wherein:

E¹ is N(R⁴)₂ where R⁴ at each occurrence is selected from hydrogen, benzyl, $C_{1-6}$alkyl, $C_{3-7}$ cycloakyl, methoxy$C_{1-4}$alkyl; and E² is morpholinyl;

R² is selected from NHR⁵, where R⁵ is selected from benz[d]thiazol-2-yl, 1,5-dimethyl-2-phenyl-1,2-dihydropyrazol-3-on-4-yl, 2-phenyl-2,5-dihydro-1H-pyrazol-3-yl, pyrimidin-4-yl, tetrahydrofuran-2-ylmethyl, 2-phenylpropyl, and 1-phenylethyl;

R³ is selected from $C_{1-6}$alkyl, phenoxy$C_{1-3}$alkyl or phenyl substituted with E⁵, where E⁵ is selected from hydrogen, halogen, $C_{1-6}$alkoxy, $C_{3-7}$cycloalkyl, morpholinyl, $C_{1-4}$perfluoroalkyl, NH$C_{1-3}$alkyl, and N($C_{1-3}$alkyl)₂.

9. A compound according to claim 8 having a structure in accord wit structural diagram II, III or IV,

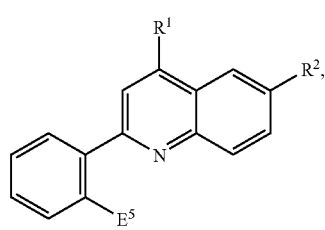

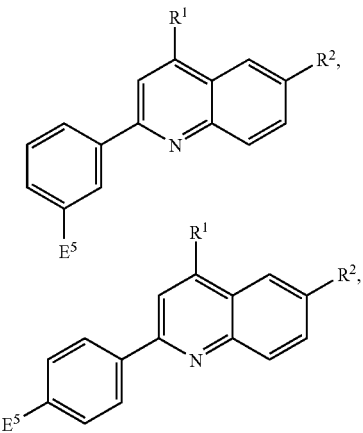

wherein R¹, R² and E⁵ are as defined in claim 8.

10. A compound according to claim 9 having a structure in accord with structural diagram III wherein:

E⁵ is halogen and R¹ and R² are as defined in claim 9.

11. A compound according to claim 10 wherein:

E⁵ is fluoro.

12. A method for the treatment of pain in a subject suffering therefrom, comprising administering to said subject a pain-ameliorating effective amount of a compound according to claim 8.

13. A pharmaceutical composition comprising a therapeutically-effective amount of a compound according to claim 8 together with a pharmaceutically-acceptable excipient or diluent.

14. A method for preparing a compound according to claim 8, said method comprising:

a) preparing 3-substituted-3-oxo-propionic acid ethyl ester (β-keto ester) according to structural diagram V as follows:

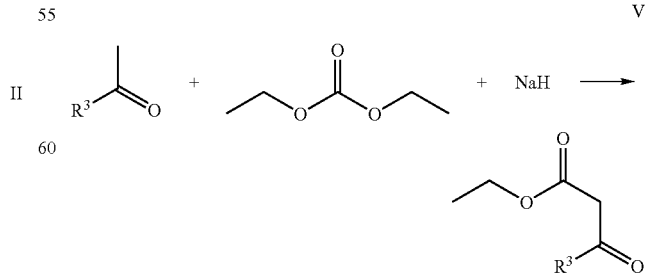

wherein R³ is as defined in claim 8;

b) converting said β-keto ester of structural diagram V to an enamine according to structural diagram VI as follows

VI

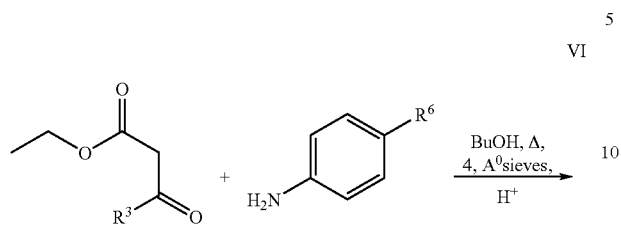

wherein $R^6$ is a group selected from —NH—CO—CH$_3$, NO$_2$, and Br;

c) cyclizing said enamine of structural diagram VI to form a compound according to structural diagram VII as follows

VII

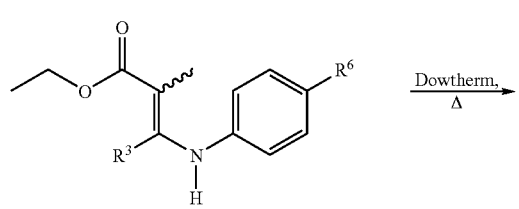

-continued

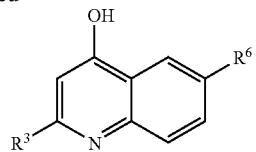

d) when $R^6$ is —NH—CO—CH$_3$, converting a compound of structural diagram VII to a compound according to structural diagram I by the process of the following scheme:

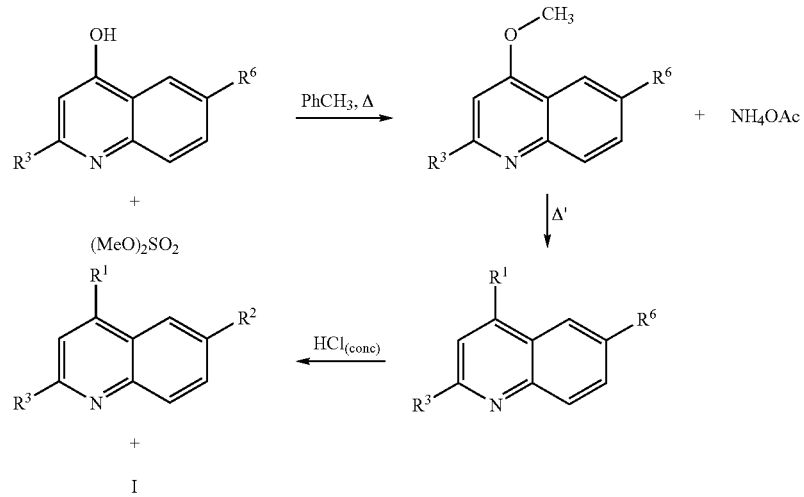

or, when $R^6$ is —NO$_2$, converting a compound of structural diagram VII to a compound according to structural diagram I wherein $R^1$ and $R^2$ are both NH$_2$, by the process of the following scheme:

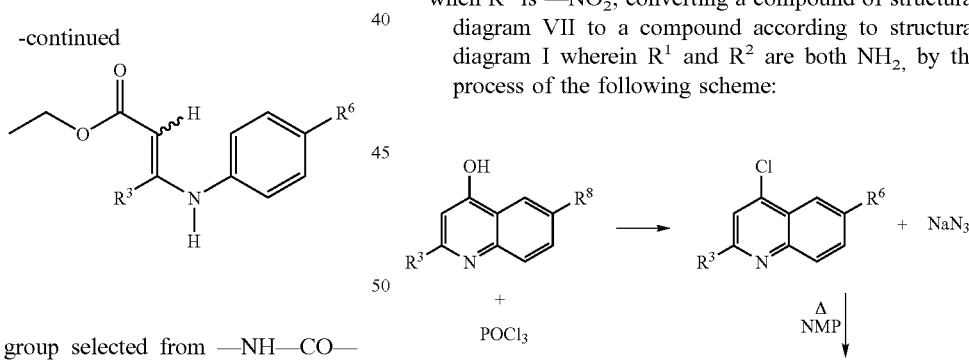

or, when $R^6$ is —Br, converting a compound of structural diagram VII to a compound according to structural diagram I wherein $R^2$ is $E^3$, by the process of the following scheme:

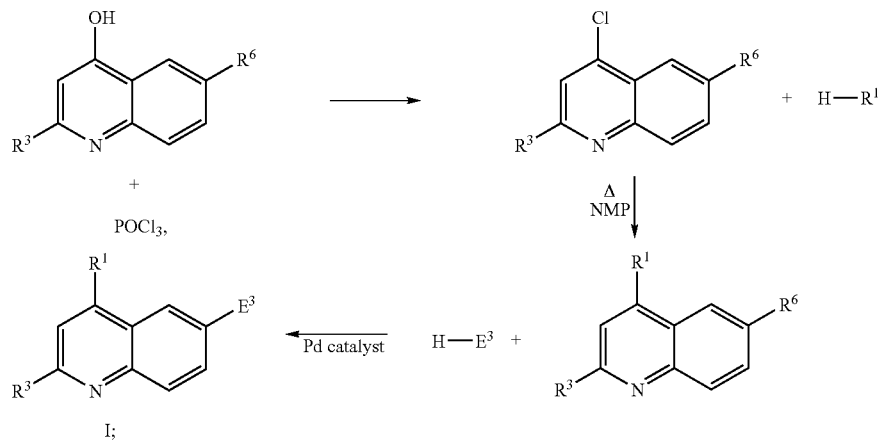

wherein, if necessary, in steps a), b), c) and d) any functional group is protected with a protecting group, and thereafter,
e) removing any said protecting group;
f) convening one compound according to structural diagram I to another compound according to structural diagram I by procedures described in Methods A through L herein, and g) purifying said compound of structural diagram I to the extent necessary and, if necessary, forming a pharmaceutically-acceptable salt.

* * * * *